US011123117B1

(12) United States Patent
Sweeney et al.

(10) Patent No.: US 11,123,117 B1
(45) Date of Patent: Sep. 21, 2021

(54) SURGICAL FIXATION SYSTEM AND RELATED METHODS

(71) Applicant: NuVasive, Inc., San Diego, CA (US)

(72) Inventors: Thomas Sweeney, La Jolla, CA (US); Chad Grant, Escondido, CA (US); Spencer Pettine, San Diego, CA (US); Ryan Donahoe, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 604 days.

(21) Appl. No.: 13/666,933

(22) Filed: Nov. 1, 2012

Related U.S. Application Data

(60) Provisional application No. 61/554,430, filed on Nov. 1, 2011.

(51) Int. Cl.
A61B 17/80 (2006.01)

(52) U.S. Cl.
CPC ........ *A61B 17/8004* (2013.01); *A61B 17/808* (2013.01); *A61B 17/8023* (2013.01)

(58) Field of Classification Search
CPC . A61B 17/7058; A61B 17/7059; A61B 17/80; A61B 17/8004; A61B 17/8009; A61B 17/8014; A61B 17/8019; A61B 17/8023; A61B 17/8033; A61B 17/8038; A61B 17/8042; A61B 17/8047; A61B 17/8052; A61B 17/844; A61B 17/8695
USPC ........................................ 606/280–299, 86 B
See application file for complete search history.

(56) References Cited

U.S. PATENT DOCUMENTS

| | | | |
|---|---|---|---|
| 2,406,832 A | 9/1946 | Hardinge | |
| 2,460,470 A | 2/1949 | Perry | |
| 2,486,303 A | 10/1949 | Longfellow | |
| 3,016,077 A | 1/1962 | Yocum | |
| 3,900,025 A * | 8/1975 | Barnes, Jr. | 606/71 |
| 4,187,840 A | 2/1980 | Watanabe | |
| 5,092,893 A | 3/1992 | Smith | |
| 5,108,395 A | 4/1992 | Laurain | |
| 5,129,903 A * | 7/1992 | Luhr et al. | 606/71 |
| 5,261,910 A * | 11/1993 | Warden | A61B 17/7059 606/292 |
| 5,364,399 A | 11/1994 | Lowery | |
| 5,520,690 A | 5/1996 | Errico | |
| 5,531,554 A | 7/1996 | Jeanson | |
| 5,616,142 A * | 4/1997 | Yuan et al. | 606/71 |
| 5,716,357 A | 2/1998 | Rogozinski | |
| 5,728,099 A | 3/1998 | Tellman | |
| 5,785,713 A | 7/1998 | Jobe | |

(Continued)

FOREIGN PATENT DOCUMENTS

AU 2006252101 A1 1/2007
CN 201019820 Y 2/2008
(Continued)

*Primary Examiner* — Lynnsy M Summitt
(74) *Attorney, Agent, or Firm* — Hoffman Warnick LLC

(57) ABSTRACT

A surgical fixation system including a base plate, a plurality of anchors and a locking element. The base plate has at least a pair of fixation apertures configured to receive at least a portion of the anchors therethrough. The fixation apertures are located within the base plate such that upon proper placement of the base plate within a surgical target site, one of the fixation apertures is positioned over a first bone segment (e.g., a first vertebral body), and the other fixation aperture is positioned over a second bone segment (e.g., a second vertebral body).

19 Claims, 22 Drawing Sheets

(56) References Cited

U.S. PATENT DOCUMENTS

| | | | |
|---|---|---|---|
| 5,827,286 A * | 10/1998 | Incavo et al. | 606/71 |
| 5,851,207 A | 12/1998 | Cesarone | |
| 5,902,304 A | 5/1999 | Walker | |
| 5,931,838 A | 8/1999 | Vito | |
| 5,941,881 A | 8/1999 | Barnes | |
| 5,947,970 A | 9/1999 | Schmelzeisen | |
| 5,954,722 A | 9/1999 | Bono | |
| 5,957,927 A | 9/1999 | Magee | |
| 5,964,762 A * | 10/1999 | Biedermann et al. | 606/71 |
| 5,979,907 A | 11/1999 | Udagawa | |
| 6,053,919 A | 4/2000 | Talos | |
| 6,066,142 A * | 5/2000 | Serbousek et al. | 606/96 |
| 6,156,037 A | 12/2000 | LeHuec | |
| 6,183,476 B1 | 2/2001 | Gerhardt | |
| 6,193,721 B1 | 2/2001 | Michelson | |
| 6,235,033 B1 | 5/2001 | Brace | |
| 6,241,731 B1 | 6/2001 | Fiz | |
| 6,258,089 B1 | 7/2001 | Campbell | |
| 6,261,291 B1 | 7/2001 | Talaber | |
| 6,299,616 B1 | 10/2001 | Beger | |
| 6,302,883 B1 * | 10/2001 | Bono | A61B 17/7058 606/291 |
| 6,306,136 B1 * | 10/2001 | Baccelli | 606/279 |
| 6,306,139 B1 | 10/2001 | Fuentes | |
| 6,331,179 B1 * | 12/2001 | Freid | A61B 17/7059 606/279 |
| 6,332,887 B1 | 12/2001 | Knox | |
| 6,361,537 B1 | 3/2002 | Anderson | |
| 6,364,880 B1 | 4/2002 | Michelson | |
| 6,402,756 B1 * | 6/2002 | Ralph | A61B 17/7059 606/287 |
| 6,436,103 B1 | 8/2002 | Suddaby | |
| 6,454,769 B2 * | 9/2002 | Wagner | A61B 17/7059 606/279 |
| 6,458,131 B1 * | 10/2002 | Ray | A61B 17/7044 606/261 |
| 6,533,786 B1 | 3/2003 | Needham | |
| 6,565,571 B1 | 5/2003 | Jackowski | |
| 6,592,578 B2 | 7/2003 | Henniges | |
| 6,602,255 B1 | 8/2003 | Campbell | |
| 6,602,257 B1 | 8/2003 | Thramann | |
| 6,610,091 B1 | 8/2003 | Reiley | |
| 6,613,053 B1 | 9/2003 | Collins | |
| 6,613,055 B2 | 9/2003 | Di Emidio | |
| 6,645,208 B2 * | 11/2003 | Apfelbaum | A61B 17/80 606/281 |
| 6,648,891 B2 | 11/2003 | Kim | |
| 6,682,563 B2 * | 1/2004 | Scharf | A61F 2/4455 606/247 |
| 6,689,134 B2 * | 2/2004 | Ralph et al. | 606/71 |
| 6,692,503 B2 | 2/2004 | Foley | |
| 6,699,249 B2 | 3/2004 | Schläpfer | |
| 6,730,127 B2 | 5/2004 | Michelson | |
| 6,736,819 B2 | 5/2004 | Tipirneni | |
| 6,764,489 B2 * | 7/2004 | Ferree | A61B 17/7059 606/279 |
| 6,793,658 B2 | 9/2004 | LeHuec | |
| 6,852,113 B2 * | 2/2005 | Nathanson et al. | 606/71 |
| 6,855,147 B2 | 2/2005 | Harrington | |
| 6,884,242 B2 | 4/2005 | LeHuec | |
| 6,893,444 B2 | 5/2005 | Orbay | |
| 6,896,676 B2 | 5/2005 | Zubok | |
| 6,916,323 B2 | 7/2005 | Kitchens | |
| 6,989,012 B2 | 1/2006 | Lehuec | |
| 7,001,389 B1 | 2/2006 | Navarro | |
| 7,011,665 B2 | 3/2006 | Null | |
| 7,033,377 B2 * | 4/2006 | Miller, III | 606/213 |
| 7,041,105 B2 * | 5/2006 | Michelson | 606/70 |
| 7,044,952 B2 * | 5/2006 | Michelson | 606/71 |
| 7,048,739 B2 | 5/2006 | Konieczynski | |
| 7,060,067 B2 | 6/2006 | Needham | |
| 7,090,676 B2 * | 8/2006 | Huebner et al. | 606/71 |
| 7,097,645 B2 * | 8/2006 | Michelson | 606/71 |
| 7,112,202 B2 * | 9/2006 | Michelson | 606/71 |
| 7,115,130 B2 * | 10/2006 | Michelson | 606/71 |
| 7,118,573 B2 * | 10/2006 | Michelson | A61B 17/7059 606/70 |
| 7,175,623 B2 | 2/2007 | Thramann | |
| 7,175,624 B2 | 2/2007 | Konieczynski | |
| 7,186,254 B2 * | 3/2007 | Dinh et al. | 606/86 A |
| 7,186,256 B2 * | 3/2007 | Michelson | 606/71 |
| 7,201,753 B2 * | 4/2007 | Schlapfer et al. | 606/71 |
| 7,214,226 B2 * | 5/2007 | Alleyne | 606/86 A |
| 7,273,481 B2 * | 9/2007 | Lombardo | A61B 17/8042 606/86 A |
| 7,278,997 B1 | 10/2007 | Mueller | |
| 7,303,564 B2 | 12/2007 | Freid | |
| 7,318,825 B2 * | 1/2008 | Butler et al. | 606/71 |
| 7,322,980 B2 | 1/2008 | Roussouly | |
| 7,322,984 B2 * | 1/2008 | Doubler et al. | 606/70 |
| 7,331,961 B2 | 2/2008 | Abdou | |
| 7,399,301 B2 * | 7/2008 | Michelson | 606/71 |
| 7,479,143 B2 | 1/2009 | Suh | |
| 7,485,132 B1 | 2/2009 | McBride | |
| 7,524,325 B2 | 4/2009 | Khalili | |
| 7,547,306 B2 * | 6/2009 | Michelson | 606/71 |
| 7,572,276 B2 * | 8/2009 | Lim et al. | 606/246 |
| 7,601,175 B2 | 10/2009 | Feigenwinter | |
| 7,604,638 B2 | 10/2009 | Jacene | |
| 7,621,914 B2 * | 11/2009 | Ralph | A61B 17/80 606/280 |
| 7,621,942 B2 | 11/2009 | Piehl | |
| 7,621,943 B2 * | 11/2009 | Michelson | 606/281 |
| 7,625,378 B2 | 12/2009 | Foley | |
| 7,635,364 B2 * | 12/2009 | Barrall et al. | 606/70 |
| 7,635,366 B2 * | 12/2009 | Abdou | 606/71 |
| 7,648,506 B2 | 1/2010 | McCord | |
| 7,648,507 B2 | 1/2010 | Techiera | |
| 7,666,185 B2 * | 2/2010 | Ryan et al. | 606/71 |
| 7,695,473 B2 * | 4/2010 | Ralph | A61B 17/8023 606/71 |
| 7,699,880 B2 | 4/2010 | Orbay | |
| 7,704,250 B2 * | 4/2010 | Michelson | 606/71 |
| 7,704,251 B2 * | 4/2010 | Huebner et al. | 606/71 |
| 7,704,255 B2 * | 4/2010 | Michelson | 606/86 B |
| 7,727,265 B2 * | 6/2010 | Paul | 606/281 |
| 7,736,380 B2 | 6/2010 | Johnston | |
| 7,740,630 B2 * | 6/2010 | Michelson | 606/71 |
| 7,749,256 B2 * | 7/2010 | Farris et al. | 606/282 |
| 7,763,056 B2 * | 7/2010 | Dalton | 606/282 |
| 7,776,047 B2 | 8/2010 | Fanger | |
| 7,789,899 B2 * | 9/2010 | Markworth et al. | 606/286 |
| 7,803,157 B2 * | 9/2010 | Michelson | 606/71 |
| 7,811,285 B2 * | 10/2010 | Michelson | 606/71 |
| 7,824,432 B2 * | 11/2010 | Michelson | 606/281 |
| 7,846,163 B2 | 12/2010 | Fourcault | |
| 7,857,837 B2 | 12/2010 | Lieponis | |
| 7,857,839 B2 | 12/2010 | Duong | |
| 7,862,597 B2 * | 1/2011 | Gause et al. | 606/290 |
| 7,875,061 B2 * | 1/2011 | Bolger et al. | 606/280 |
| 7,883,510 B2 | 2/2011 | Kim | |
| 7,901,433 B2 | 3/2011 | Forton | |
| 7,901,440 B2 * | 3/2011 | Ibrahim et al. | 606/282 |
| 7,909,848 B2 | 3/2011 | Patel | |
| 7,909,860 B2 | 3/2011 | Rathbun | |
| 7,914,562 B2 | 3/2011 | Zielinski | |
| 7,935,123 B2 | 5/2011 | Fanger | |
| 7,935,137 B2 | 5/2011 | Gorhan | |
| 7,942,913 B2 | 5/2011 | Ziolo | |
| 7,951,151 B2 | 5/2011 | Butler | |
| 7,955,362 B2 | 6/2011 | Erickson | |
| 7,963,980 B1 | 6/2011 | Freeman | |
| 7,963,982 B2 | 6/2011 | Kirschman | |
| 7,985,224 B2 * | 7/2011 | Michelson | 606/71 |
| 7,988,691 B2 | 8/2011 | Schulze | |
| 7,993,380 B2 * | 8/2011 | Hawkes | 606/282 |
| 7,998,179 B2 * | 8/2011 | Lindemann et al. | 606/282 |
| 8,002,809 B2 | 8/2011 | Baynham | |
| 8,048,114 B2 | 11/2011 | Tornier | |
| 8,066,749 B2 * | 11/2011 | Winslow et al. | 606/281 |
| 8,066,751 B2 | 11/2011 | Podgorski | |
| 8,070,749 B2 * | 12/2011 | Stern | 606/71 |
| 8,083,781 B2 | 12/2011 | Reimels | |

(56) References Cited

U.S. PATENT DOCUMENTS

| | | | |
|---|---|---|---|
| 8,100,955 B2* | 1/2012 | Blain ................ A61B 17/7059 606/289 |
| 8,109,934 B2 | 2/2012 | Guenther |
| 8,114,138 B2 | 2/2012 | Nehls |
| 8,123,785 B2 | 2/2012 | Weaver |
| 8,128,628 B2* | 3/2012 | Freid et al. .................... 606/71 |
| 8,152,838 B2* | 4/2012 | Ensign ............... A61B 17/8047 606/280 |
| 8,167,917 B2* | 5/2012 | Chin et al. ................... 606/280 |
| 8,167,919 B2* | 5/2012 | Foley et al. .................. 606/290 |
| 8,172,854 B2 | 5/2012 | Blain |
| 8,172,885 B2 | 5/2012 | Songer |
| 8,182,533 B2 | 5/2012 | Perkins |
| 8,197,405 B2 | 6/2012 | Lindsay |
| 8,197,484 B2 | 6/2012 | Sato |
| 8,206,390 B2* | 6/2012 | Lindemann ..................... 606/71 |
| 8,211,151 B2 | 7/2012 | Schwab |
| 8,211,154 B2 | 7/2012 | Fisher |
| 8,216,312 B2* | 7/2012 | Gray .................. A61B 17/7059 606/249 |
| 8,226,693 B2 | 7/2012 | Reimels |
| 8,226,695 B2 | 7/2012 | Moore |
| 8,231,627 B2 | 7/2012 | Huebner |
| 8,231,662 B2 | 7/2012 | Huebner |
| 8,246,662 B2 | 8/2012 | Lemoine |
| 8,262,659 B2* | 9/2012 | Ryan et al. ..................... 606/71 |
| 8,262,710 B2* | 9/2012 | Freedman et al. ............ 606/282 |
| 8,262,711 B2* | 9/2012 | Hess ............................. 606/282 |
| 8,273,111 B2* | 9/2012 | Amato et al. ................. 606/280 |
| 8,282,642 B2 | 10/2012 | McClintock |
| 8,282,675 B2* | 10/2012 | Maguire et al. .............. 606/289 |
| 8,287,550 B2 | 10/2012 | Campbell |
| 8,287,574 B2* | 10/2012 | Biyani et al. ................. 606/282 |
| 8,298,271 B2* | 10/2012 | Jacene et al. ................. 606/281 |
| 8,298,272 B2 | 10/2012 | Edie |
| 8,328,807 B2 | 12/2012 | Brigido |
| 8,328,853 B2* | 12/2012 | Ibrahim et al. ............... 606/282 |
| 8,328,856 B1* | 12/2012 | Donahoe et al. ............. 606/294 |
| 8,348,949 B2 | 1/2013 | Butler |
| 8,353,939 B2 | 1/2013 | Anderson |
| 8,372,081 B1* | 2/2013 | Schafer et al. ................. 606/90 |
| 8,372,121 B2 | 2/2013 | Capote |
| 8,388,663 B2* | 3/2013 | Bush et al. .................... 606/282 |
| 8,394,130 B2 | 3/2013 | Orbay |
| 8,414,616 B2 | 4/2013 | Berrevoets |
| 8,425,513 B2* | 4/2013 | Frankie et al. ................. 606/63 |
| 8,425,573 B2 | 4/2013 | Erickson |
| 8,430,929 B2 | 4/2013 | Tribus |
| 8,454,694 B2 | 6/2013 | Armstrong |
| 8,480,716 B2* | 7/2013 | Perrow et al. ................ 606/286 |
| 8,480,747 B2 | 7/2013 | Melkent |
| 8,491,593 B2 | 7/2013 | Prien |
| 8,496,665 B2 | 7/2013 | Cavallazzi |
| 8,500,783 B2 | 8/2013 | Baynham |
| 8,500,811 B2 | 8/2013 | Blain |
| 8,506,607 B2 | 8/2013 | Eckhof |
| 8,518,089 B2* | 8/2013 | Gabele ......................... 606/282 |
| 8,523,919 B2 | 9/2013 | Huebner |
| 8,535,354 B2 | 9/2013 | Cummins |
| 8,551,430 B2 | 10/2013 | Brück |
| 8,556,895 B2* | 10/2013 | Stern .............................. 606/71 |
| 8,556,944 B2 | 10/2013 | Dube |
| 8,574,270 B2* | 11/2013 | Hess et al. .................... 606/282 |
| 8,574,271 B2 | 11/2013 | Crainich |
| 8,608,783 B2 | 12/2013 | Graham |
| 8,623,019 B2 | 1/2014 | Perrow |
| 8,636,738 B2* | 1/2014 | McClintock et al. .......... 606/71 |
| 8,647,371 B2 | 2/2014 | Black |
| 8,679,160 B2 | 3/2014 | Jensen |
| 8,696,721 B2* | 4/2014 | Blain ............................ 606/319 |
| 8,702,762 B2 | 4/2014 | Jacene |
| 8,728,082 B2 | 5/2014 | Fritzinger |
| 8,728,127 B2 | 5/2014 | Stewart |
| 8,728,128 B2* | 5/2014 | Hawkes ............. A61B 17/7059 606/290 |
| 8,740,915 B2 | 6/2014 | Niederberger |
| 8,747,442 B2* | 6/2014 | Orbay et al. .................. 606/281 |
| 8,753,349 B2* | 6/2014 | Cohen et al. ................. 606/105 |
| 8,758,347 B2* | 6/2014 | Weiner et al. .................. 606/71 |
| 8,758,417 B2 | 6/2014 | Anderson |
| 8,784,419 B2* | 7/2014 | Overes et al. .................. 606/71 |
| 8,795,277 B2 | 8/2014 | Leuenberger |
| 8,795,340 B2* | 8/2014 | Weiman ............. A61B 17/8042 606/289 |
| 8,801,760 B2* | 8/2014 | Amato et al. ................. 606/280 |
| 8,808,307 B2 | 8/2014 | Robinson |
| 8,814,869 B2* | 8/2014 | Freid et al. ..................... 606/71 |
| 8,821,552 B2* | 9/2014 | Reitzig ............... A61B 17/7059 606/282 |
| 8,834,533 B2* | 9/2014 | Michelson .................... 606/280 |
| 8,870,932 B2 | 10/2014 | Robinson |
| 8,915,918 B2 | 12/2014 | Graham |
| 8,956,415 B2 | 2/2015 | Cowan |
| 8,986,353 B2 | 3/2015 | Johnson |
| 9,095,387 B2* | 8/2015 | Angelucci .......... A61B 17/7059 |
| 9,414,865 B2* | 8/2016 | Duggal ............... A61B 17/808 |
| 9,622,799 B2* | 4/2017 | Orbay ................ A61B 17/8085 |
| 2002/0120273 A1* | 8/2002 | Needham et al. ............... 606/61 |
| 2003/0040746 A1 | 2/2003 | Mitchell |
| 2003/0105462 A1 | 6/2003 | Haider |
| 2003/0135216 A1 | 7/2003 | Sevrain |
| 2003/0229348 A1* | 12/2003 | Sevrain ........................... 606/70 |
| 2003/0236528 A1 | 12/2003 | Thramann |
| 2004/0006343 A1* | 1/2004 | Sevrain ........................... 606/61 |
| 2004/0019353 A1* | 1/2004 | Freid et al. ..................... 606/69 |
| 2004/0030336 A1 | 2/2004 | Khanna |
| 2004/0097925 A1 | 5/2004 | Boehm |
| 2004/0102776 A1* | 5/2004 | Huebner ......................... 606/69 |
| 2004/0106924 A1* | 6/2004 | Ralph et al. .................... 606/71 |
| 2004/0158250 A1* | 8/2004 | Chappuis ........................ 606/69 |
| 2004/0167521 A1* | 8/2004 | De Windt ...................... 606/69 |
| 2004/0172040 A1 | 9/2004 | Heggeness |
| 2004/0176773 A1 | 9/2004 | Zubok |
| 2004/0186570 A1 | 9/2004 | Rapp |
| 2004/0204712 A1* | 10/2004 | Kolb .................. A61B 17/1728 606/71 |
| 2004/0210232 A1 | 10/2004 | Patel |
| 2005/0004573 A1* | 1/2005 | Abdou ........................... 606/61 |
| 2005/0010221 A1 | 1/2005 | Dalton |
| 2005/0010227 A1* | 1/2005 | Paul ............................... 606/71 |
| 2005/0015093 A1 | 1/2005 | Suh |
| 2005/0049595 A1* | 3/2005 | Suh et al. ....................... 606/69 |
| 2005/0059970 A1* | 3/2005 | Kolb .............................. 606/69 |
| 2005/0065521 A1 | 3/2005 | Steger |
| 2005/0131412 A1 | 6/2005 | Olevsky |
| 2005/0137606 A1 | 6/2005 | Binder |
| 2005/0177160 A1 | 8/2005 | Baynham |
| 2005/0216008 A1 | 9/2005 | Zwirnmann |
| 2005/0240198 A1* | 10/2005 | Albertson .......... A61B 17/8076 606/103 |
| 2005/0277939 A1 | 12/2005 | Miller |
| 2005/0288673 A1* | 12/2005 | Catbagan ........... A61B 17/7007 606/281 |
| 2006/0009770 A1 | 1/2006 | Speirs |
| 2006/0058796 A1 | 3/2006 | Hartdegen |
| 2006/0122606 A1* | 6/2006 | Wolgen .......................... 606/71 |
| 2006/0149289 A1 | 7/2006 | Winslow |
| 2006/0155283 A1 | 7/2006 | Doherty |
| 2006/0189989 A1 | 8/2006 | Bert |
| 2006/0195101 A1* | 8/2006 | Stevens .......................... 606/70 |
| 2006/0200134 A1* | 9/2006 | Freid et al. ..................... 606/61 |
| 2006/0221247 A1 | 10/2006 | Doyen |
| 2006/0271052 A1* | 11/2006 | Stern .............................. 606/69 |
| 2007/0123881 A1* | 5/2007 | Ralph et al. .................... 606/69 |
| 2007/0123884 A1 | 5/2007 | Abdou |
| 2007/0162019 A1 | 7/2007 | Burns |
| 2007/0203492 A1* | 8/2007 | Needham et al. ............... 606/61 |
| 2008/0097443 A1 | 4/2008 | Dixon |
| 2008/0097443 A1* | 4/2008 | Campbell ....................... 606/69 |
| 2008/0097445 A1 | 4/2008 | Weinstein |
| 2008/0114361 A1* | 5/2008 | Butler et al. ................... 606/69 |
| 2008/0147124 A1* | 6/2008 | Haidukewych et al. ..... 606/280 |
| 2008/0147125 A1* | 6/2008 | Colleran et al. .............. 606/280 |
| 2008/0154312 A1* | 6/2008 | Colleran et al. .............. 606/283 |

(56) References Cited

U.S. PATENT DOCUMENTS

| | | | |
|---|---|---|---|
| 2008/0161862 A1* | 7/2008 | Ensign | 606/303 |
| 2008/0177330 A1* | 7/2008 | Ralph | A61B 17/8038 606/290 |
| 2008/0215097 A1* | 9/2008 | Ensign | A61B 17/7059 606/282 |
| 2008/0234680 A1* | 9/2008 | Zaiser et al. | 606/71 |
| 2008/0269753 A1 | 10/2008 | Cannestra | |
| 2008/0300631 A1* | 12/2008 | Tornier | A61B 17/808 606/246 |
| 2008/0306550 A1* | 12/2008 | Matityahu | 606/290 |
| 2009/0036894 A1 | 2/2009 | Henderson | |
| 2009/0088804 A1 | 4/2009 | Kyle | |
| 2009/0105755 A1 | 4/2009 | Capote | |
| 2009/0125067 A1 | 5/2009 | Mazzuca | |
| 2009/0163960 A1 | 6/2009 | Binder | |
| 2009/0177239 A1 | 7/2009 | Castro | |
| 2009/0210008 A1* | 8/2009 | Butler et al. | 606/280 |
| 2009/0216282 A1* | 8/2009 | Blake et al. | 606/286 |
| 2009/0264886 A1* | 10/2009 | Stern | 606/70 |
| 2009/0275947 A1* | 11/2009 | Graham et al. | 606/71 |
| 2009/0281543 A1 | 11/2009 | Orbay | |
| 2009/0287249 A1 | 11/2009 | Reynolds | |
| 2009/0312801 A1 | 12/2009 | Lemoine | |
| 2010/0004691 A1* | 1/2010 | Amato | A61B 17/1728 606/280 |
| 2010/0016901 A1 | 1/2010 | Robinson | |
| 2010/0057127 A1* | 3/2010 | McGuire et al. | 606/246 |
| 2010/0057134 A1 | 3/2010 | Lowry | |
| 2010/0063505 A1 | 3/2010 | Frigg | |
| 2010/0076500 A1 | 3/2010 | Bray | |
| 2010/0094358 A1 | 4/2010 | Moore | |
| 2010/0100131 A1 | 4/2010 | Wallenstein | |
| 2010/0100138 A1 | 4/2010 | Reynolds | |
| 2010/0145386 A1 | 6/2010 | Greenhalgh | |
| 2010/0152737 A1* | 6/2010 | Ralph et al. | 606/71 |
| 2010/0191291 A1 | 7/2010 | Phan | |
| 2010/0198221 A1 | 8/2010 | Hearn | |
| 2010/0211075 A1 | 8/2010 | Stone | |
| 2010/0228297 A1 | 9/2010 | Bray | |
| 2010/0324559 A1* | 12/2010 | Ralph et al. | 606/71 |
| 2011/0022049 A1 | 1/2011 | Huebner | |
| 2011/0098751 A1 | 4/2011 | Ani | |
| 2011/0106085 A1 | 5/2011 | Null | |
| 2011/0106087 A1 | 5/2011 | Gamache | |
| 2011/0106183 A1 | 5/2011 | Dell'oca | |
| 2011/0213420 A1 | 9/2011 | Medoff | |
| 2011/0224734 A1* | 9/2011 | Schelling | 606/286 |
| 2011/0313468 A1 | 12/2011 | Robinson | |
| 2011/0319943 A1 | 12/2011 | Donahoe | |
| 2012/0016427 A1 | 1/2012 | Stindel | |
| 2012/0022600 A1 | 1/2012 | Overes | |
| 2012/0078373 A1 | 3/2012 | Gamache | |
| 2012/0083846 A1* | 4/2012 | Wallenstein et al. | 606/279 |
| 2012/0136392 A1 | 5/2012 | Keegan | |
| 2012/0158061 A1 | 6/2012 | Koch | |
| 2012/0158069 A1 | 6/2012 | Abrahams | |
| 2012/0172987 A1 | 7/2012 | Phillips | |
| 2012/0179207 A1 | 7/2012 | Mekhail | |
| 2012/0232596 A1 | 9/2012 | Ribeiro | |
| 2012/0265021 A1 | 10/2012 | Nottmeier | |
| 2012/0265203 A1* | 10/2012 | Angelucci et al. | 606/70 |
| 2012/0271310 A1 | 10/2012 | McGee | |
| 2012/0271311 A1* | 10/2012 | Hearn | 606/71 |
| 2012/0271359 A1 | 10/2012 | Stevenson | |
| 2012/0283782 A1* | 11/2012 | Ryan et al. | 606/279 |
| 2012/0316562 A1 | 12/2012 | Costa | |
| 2012/0316606 A1 | 12/2012 | Farin | |
| 2013/0046348 A1 | 2/2013 | Black | |
| 2013/0060288 A1 | 3/2013 | Rodgers | |
| 2013/0096633 A1* | 4/2013 | Black et al. | 606/289 |
| 2013/0103104 A1* | 4/2013 | Krupp et al. | 606/86 B |
| 2013/0116733 A1* | 5/2013 | Stoll, Jr. | 606/282 |
| 2013/0165934 A1* | 6/2013 | Ibrahim et al. | 606/71 |
| 2013/0172939 A1* | 7/2013 | Ziolo et al. | 606/279 |
| 2013/0190825 A1* | 7/2013 | Perrow et al. | 606/281 |
| 2013/0204249 A1 | 8/2013 | Zhao | |
| 2013/0261673 A1* | 10/2013 | Hawkins | A61B 17/7044 606/286 |
| 2013/0296941 A1* | 11/2013 | Perrow et al. | 606/281 |
| 2013/0304067 A1* | 11/2013 | Hess et al. | 606/71 |
| 2014/0039564 A1* | 2/2014 | Hess et al. | 606/294 |
| 2014/0128873 A1* | 5/2014 | McClintock et al. | 606/71 |
| 2014/0128924 A1* | 5/2014 | Perrow et al. | 606/287 |
| 2014/0214036 A1* | 7/2014 | Weiner et al. | 606/71 |
| 2014/0243828 A1 | 8/2014 | Heiney | |
| 2014/0249585 A1 | 9/2014 | Knoepfle | |
| 2014/0249587 A1* | 9/2014 | Cawley et al. | 606/291 |
| 2014/0276829 A1* | 9/2014 | Hershgold et al. | 606/71 |

FOREIGN PATENT DOCUMENTS

| | | |
|---|---|---|
| CN | 201257042 Y | 6/2009 |
| DE | 867422 C | 2/1953 |
| DE | 2808971 A1 | 9/1979 |
| DE | 3342293 A1 | 8/1984 |
| DE | 8512040 U1 | 6/1985 |
| DE | 4209010 A1 | 9/1993 |
| DE | 19754869 A1 | 6/1999 |
| DE | 19914387 A1 | 10/2000 |
| DE | 202005019863 U1 | 3/2006 |
| EP | 0151892 A1 | 8/1985 |
| EP | 0773004 A1 | 5/1997 |
| EP | 0867149 A1 | 9/2000 |
| EP | 1997449 A2 | 12/2008 |
| FR | 2720623 A1 | 12/1995 |
| FR | 2728454 A1 | 6/1996 |
| FR | 2738475 A1 | 3/1997 |
| FR | 2828643 A1 | 2/2003 |
| FR | 2855041 A1 | 11/2004 |
| IN | 3071CHE2007 | 7/2009 |
| IN | 1779CHE2007 | 9/2009 |
| IN | 2070CHE2008 | 11/2009 |
| JP | 2013066649 A | 4/2013 |
| KR | 20000024539 A | 5/2000 |
| KR | 20050023434 A | 3/2005 |
| SU | 1762907 A1 | 9/1992 |
| WO | WO-93006789 | 4/1993 |
| WO | WO-95011632 | 5/1995 |
| WO | WO-95026164 | 10/1995 |
| WO | WO-2002080791 | 10/2002 |
| WO | WO-2004017837 | 3/2004 |
| WO | WO-2004112627 | 12/2004 |
| WO | WO-2005037078 | 4/2005 |
| WO | WO-2005053553 | 6/2005 |
| WO | WO-2006111852 | 10/2006 |
| WO | WO-2008029142 | 3/2008 |
| WO | WO-2008029143 | 3/2008 |
| WO | WO-2009039430 | 3/2009 |
| WO | WO-2009055537 | 4/2009 |
| WO | WO-2009091770 | 7/2009 |
| WO | WO-2009105066 | 8/2009 |
| WO | WO-2010061410 | 6/2010 |
| WO | WO-2010144636 | 12/2010 |
| WO | WO-2011036182 | 3/2011 |
| WO | WO-2012041914 | 4/2012 |
| WO | WO-2012048480 | 4/2012 |
| WO | WO-2012048481 | 4/2012 |

\* cited by examiner

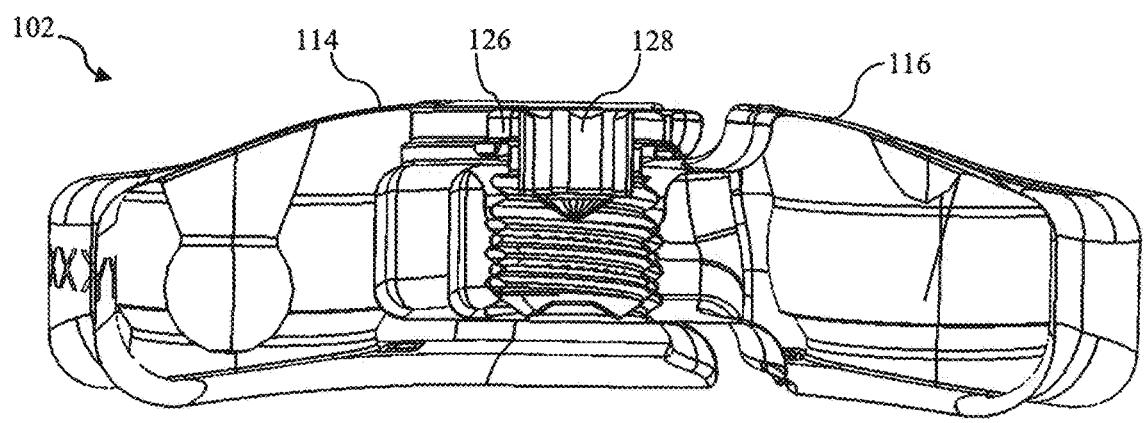
FIG. 18
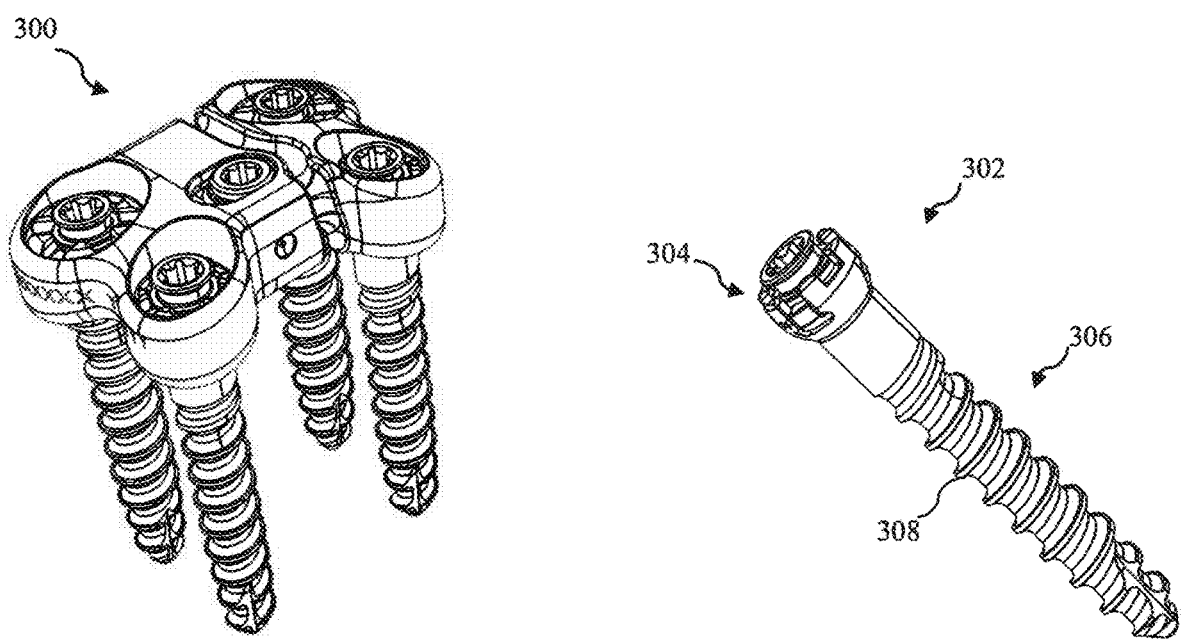
FIG. 19
FIG. 20

SURGICAL FIXATION SYSTEM AND RELATED METHODS

CROSS-REFERENCE TO RELATED APPLICATIONS

The present application is a nonprovisional patent application claiming the benefit of priority under 35 U.S.C. § 119(e) from U.S. Provisional Patent Application Ser. No. 61/554,430, filed on Nov. 1, 2011, the entire contents of which is hereby expressly incorporated by reference into this disclosure as if set forth fully herein.

FIELD OF THE INVENTION

The present invention relates generally to spinal surgery, and more particularly, to systems and methods for repairing and/or reconstructing skeletal structures.

DISCUSSION OF THE PRIOR ART

Each year millions of people suffer from back pain arising from defects in the intervertebral space. Commonly, surgical interventions directed at promoting fusion across the affected joint are employed to permanently provide long term pain relief to the patient. Typically, such fusion surgeries involve performing a partial or complete discectomy to prepare the disc space, and then implanting a natural or synthetic intervertebral fusion implant within the prepared disc space. Supplemental fixation, such as bone plates (implanted on the anterior or posterior aspect of the spine) or rod systems (implanted on the posterior aspect of the spine) may be further employed to provide stability across the affected joint while the body goes through the fusion process. Plate implants have been used for many years to aid in the promotion of fusion across affected vertebral disc spaces through stabilization of the joint. These spinal fixation plates are directed at complete immobilization of the affected joint while affording the optional benefit of restricting fusion inducing materials (such as bone grafts) within the joint. As a result of the fusion of adjacent vertebral bodies, the disc height between the vertebral bodies is restored, thereby reducing pain in the patient.

During a lateral access surgery performed through a minimally-invasive operative corridor, it can be a challenge to obtain the angle or exposure necessary to properly implant an anterior or posterior supplemental fixation apparatus. Often, additional incisions must be made to accommodate placement of such devices. Lateral fixation plates have been developed to address some of these difficulties, however these plates are not without their challenges. Base plates of shorter lengths facilitate the ease of insertion into and through the minimally-invasive surgical corridor, but plates of longer lengths may be required for successful performance of the procedure. Benefits of minimally invasive lateral approaches to the spine include decreased morbidity, decreased operative times, reduced blood loss, shortened hospital stays, and improved cosmesis. However, these benefits of minimally invasive procedures may not be effectuated where the length of the plate required to fix vertebral bodies does not allow for adequate insertion of the plate through the surgical corridor.

The present invention is directed at overcoming, or at least reducing the effects of, one or more of the problems set forth above.

SUMMARY OF THE INVENTION

The present application addresses these problems by providing a surgical fixation system including a base plate, a plurality of anchors, and a translating locking element that is expandable in situ. The examples shown and described herein are in the form of a base plate configured for a single-level spinal fusion, and as such the bone plate is sized and configured to span a single intervertebral space while achieving purchase within each of the vertebral bodies adjacent the single intervertebral space. However, the base plate may be provided in any number of sizes to accommodate multiple-level spinal fusions without departing from the scope of the present invention, depending upon the needs of the specific user. The base plate may also be provided in any number of shapes suitable for spanning at least one intervertebral disc space without departing from the scope of the invention. The base plate is particularly suitable for lateral insertion and placement against a lateral aspect of the vertebral bodies, however other uses are possible without departing from the scope of the present invention.

The base plate is provided with a pair of first fixation apertures configured to receive at least a portion of first bone anchors therethrough. The first fixation apertures are provided by example as large circular holes, however the first fixation apertures may be provided with any shape suitable for receiving at least a portion of the first bone anchors therethrough, including but not limited to ovoid or polygonal without departing from the scope of the present invention. The first fixation apertures are comprised of a first pocket and a second pocket and are sized and dimensioned to receive the first bone anchors. The base plate is further provided with a pair of second fixation apertures configured to receive at least a portion of second bone anchors therethrough. The second fixation apertures as generally circular holes, however the second fixation apertures may be provided with any shape suitable for receiving at least a portion of the second bone anchors therethrough, including but not limited to ovoid or polygonal without departing from the scope of the present invention. The second fixation apertures have a first pocket and a second pocket and are sized and dimensioned to receive the second bone anchors. The first and second fixation apertures are located within the base plate such that upon proper placement of the base plate within a surgical target site, one of the first and second fixation apertures are positioned over a first bone segment (e.g. a first vertebral body), and the other first and second fixation apertures are positioned over a second bone segment (e.g., a second vertebral body).

The base plate is further provided with two components: a female component and a male component. The female component comprises one first fixation aperture, one second fixation aperture, a receiving slot, and a lengthening slot. The male component comprises one first fixation aperture, one second fixation aperture, an insertion portion, and a locking aperture. The insertion portion of the male component is sized and dimensioned to snugly fit within the receiving slot of the female component. The male and female components of the base plate are securely mated to one another via the translating locking element.

In its assembled state, the base plate has a first end, a second end, a first side, and a second side. The base plate further includes a first surface and an opposing second surface. When properly positioned on a lateral aspect of a spinal column, the second surface interfaces with the bone and thus is a vertebral contacting surface. Moreover, the first end represents the cephalad-most (or top) end of the base plate, the first side represents the posterior-most (or back) side of the base plate and the second side represents the anterior-most (or front) side of the base plate. First and second ends preferably each have a radius of curvature that is approximately equal to the radius of curvature of the retractor blades of a surgical retraction system.

The second surface of the base plate may include one or more protrusions which engage the bones of the vertebral bodies, the disc space, or the vertebral spacer. This engagement prevents the base plate from moving while the plurality of bone anchors is being placed. Base plate may also have one or more engagement features for engagement with an insertion device, for example a translating plate inserter.

The first bone anchors may be, by way of example only, threaded bone screws, however other forms of anchors are possible without departing from the scope of the present invention. The bone screw comprises a screw head and a shank. The shank includes threads for threaded purchase into a bony segment (e.g. vertebral body). The screw head is comprised of an upper screw head region, a plurality of locks, a lock screw, and a bottom spherical portion.

The surgical fixation system also includes a locking mechanism for fixedly coupling the first and second bone anchors to the base plate after implantation. According to one embodiment, the fixation apertures each have a first spherical pocket and a second spherical pocket sized and dimensioned for receiving a bone screw therein. The bone screw is placed through the base plate and mates with the first spherical pocket within the base plate via the matching a bottom spherical surface of the bone screw. The bone screw has a cone of angulations in which it can be placed and still lock to the plate. Locks have a spherical inner face which fit into the second spherical pocket. Once the bone screw is fully seated within the first spherical pocket, a driver mechanism may rotate the lock screw via the inner tool engaging recess towards the interior of the of the screw head. With the locks fully engaged, further polyaxial motion of the bone screw is prevented as is unwanted backout of the bone screw.

The second bone anchors may be provided, by way of example only, in the form of bone staples, however other forms of anchors are possible without departing from the scope of the present invention. The bone staple comprises a staple head and an elongate body. The elongate body preferably includes a pointed distal tip for purchase into a bony segment (e.g., vertebral body). The bone staple has blades that run down the length of the elongate body. The flat faces of the blades (for example, in a cruciform configuration) prevent rotation of the bone staple about its central axis. Because the bone staple is not threaded, it can be impacted into the bone quickly, thereby reducing the time required for implantation. The staple head is mated and locked to the base plate via first and second spherical pockets the same way as described above for the bone screw.

In minimally invasive lateral approaches to the spine, base plates of shorter lengths facilitate the ease of insertion into and through the surgical corridor. However, depending on patient's anatomy and/or surgical requirements, base plates of longer lengths may be advantageous notwithstanding the difficulties associated with inserting a longer plate. In a preferred embodiment of the present invention, the base plate of the surgical fixation system contains an in situ lengthening feature (translating locking element) that allows the length of the base plate to be variably lengthened in situ. In the closed position, the male portion of the base plate is fully inserted into the female portion such that the set screw is maximally situated within the lengthening slot. In the open position, the male insertion portion is extended away from the female receiving slot such that at least some portion of the male insertion portion is not contained within the female receiving slot. This distance of such a non-contained portion is limited by the distance between the two ends of the lengthening slot within the translating locking element.

In a preferred embodiment, the base plate is inserted in its smallest, closed configuration via a lateral approach to lateral aspect of the spine. Once the base plate has reached the spinal target site, the plate may be lengthened until the set screw prevents any further extension within the lengthening slot. Once the desired length has been achieved, the translating locking element may be secured, thereby locking the length into position.

The base plate, anchors and/or locking components etc. may be formed of any material suitable to provide rigid fixation between two bony segments. By way of example, all may be formed of a biocompatible metal, such as titanium. The base plate may be provided with any size necessary to complete the desired spinal fixation.

The surgical fixation systems of the present invention are assembled in situ during a surgical procedure. One such example is a spinal fusion surgery. The surgical fixation systems disclosed herein are optimally used in a direct lateral surgical procedure in which the spine is approached laterally at approximately a 90° angle relative to the patient's spine. The first step in such a procedure is to create an operative corridor through the patient's skin and underlying musculature to the spinal target site, for example, a symptomatic intervertebral disc located between first and second adjacent vertebral bodies. The specific technique involved in performing this step is shown and described in commonly-owned U.S. Pat. No. 7,905,840, filed on Oct. 18, 2004, patented on Mar. 15, 2011, and entitled "Surgical Access System and Related Methods," the entire contents of which are hereby incorporated by reference into this disclosure as if set forth fully herein.

After establishment of the operative corridor to the surgical target site, the next step is to perform the necessary therapeutic technique to relieve the distress on the target disc space. For example, this may involve performing a partial or total discectomy (removing damaged or degenerative disc tissue from the intervertebral space) and then inserting a spinal fusion implant such as a bone graft (e.g., allograft, autograft, or xenograft) or synthetic fusion cage (e.g., titanium and/or PEEK) into the space. One example of a synthetic spinal fusion implant that may be used is shown and described in commonly-owned U.S. Pat. No. 7,819,891 filed on Mar. 29, 2005, issued on Apr. 5, 2011, and entitled "Systems and Methods for Spinal Fusion," the entire contents of which are hereby incorporated by reference into this disclosure as if set forth fully herein. These spinal fusion implants (natural or synthetic) may be used with or without additional fusion-inducing materials, such as an orthopedic matrix containing, for example, calcium hydroxyapatite, bone morphogenic protein (BMP), demineralized bone matrix, collagen bone graft matrix, and stem cell material, or other fusion-promoting substances placed within the spaces of the implant, while the implant is advanced into the intervertebral space.

After addressing the disc space, the surgical fixation system may be implanted. A variety of instruments may be provided to assist in the implantation of the surgical fixation system of the present invention. In accordance with the present invention, there is also provided a plate inserter for inserting the surgical fixation system, preferably from a lateral approach. The plate inserter facilitates proper insertion of the base plate as well as lengthening of the base plate in situ.

Once the base plate is properly seated within the surgical target site, the surgeon proceeds with pilot hole formation to prepare the vertebral bodies for receiving the first bone anchors. Formation of the pilot hole may be accomplished via a number of different techniques and instruments depending upon the surgeon's preference, including but not limited to using drills, taps, awls, etc. to create a pilot hole that is preferably undersized by 1 mm relative to the first bone anchors to be used in order to maximize the purchase of the bone screws within the bone.

Upon formation of the pilot hole, the bone screws and bone staples are inserted into the bone. Insertion of the bone screws may be accomplished via a number of different techniques and instruments depending on the surgeon's preference. Preferably, a driver is used to insert the bone screws and bone staples into the bone. Once the bone screws and bone anchors are implanted through the base plate and into the vertebral bodies, the locking elements on the bone screws, bone anchors, and plate may be applied to secure the base plate in place and complete the assembly of the surgical fixation system.

At this stage, the surgical fixation system is fully assembled in situ and implanted into a surgical target site. The procedure being completed, the operative corridor is closed and the incision is stitched up.

BRIEF DESCRIPTION OF THE DRAWINGS

FIG. 18 is a cross-sectional view of the base plate of the surgical fixation system of FIG. 1;

FIG. 19 is an example of a surgical fixation system according to a second embodiment of the present invention;

FIG. 20 is a perspective view of one example of a second bone anchor of the surgical fixation system of FIG. 19;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical fixation system and related methods disclosed herein boast a variety of inventive features and components that warrant patent protection, both individually and in combination.

Figure 1:
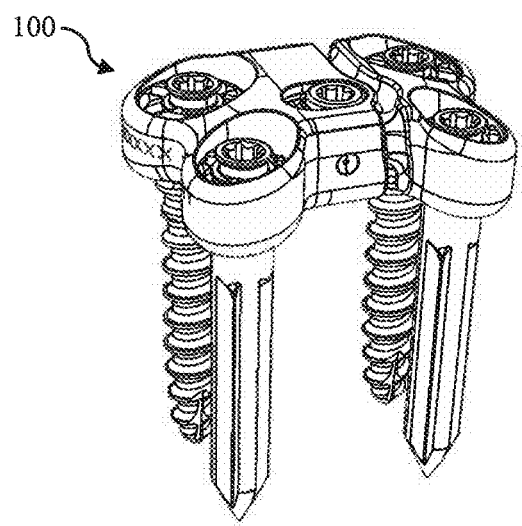
FIG. 1 is a perspective view of an example of a surgical fixation system according to one embodiment of the present invention.
Figure 2:
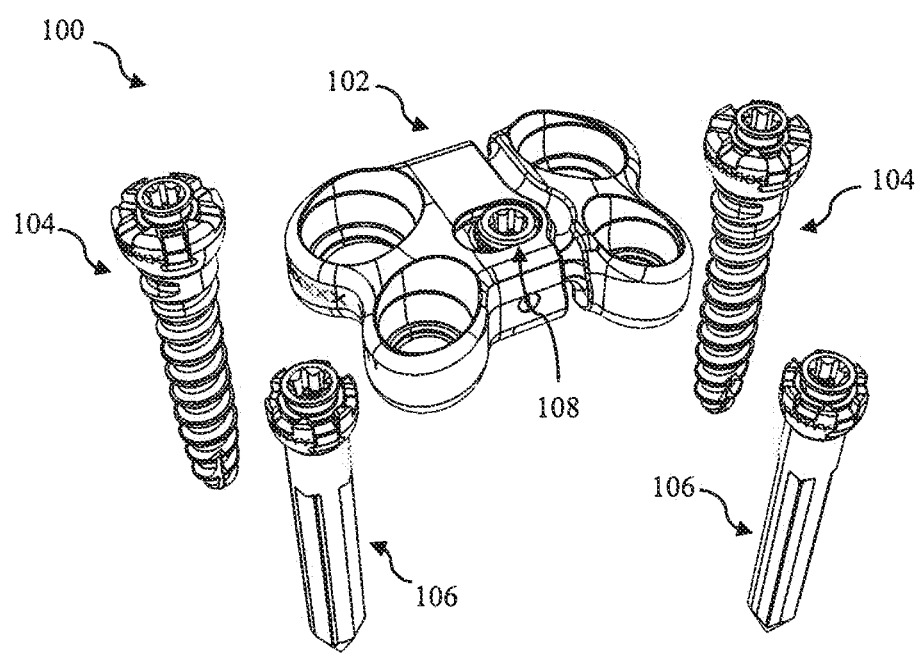
FIG. 2 is an exploded perspective view of the surgical fixation system of FIG. 1.
Figure 3:
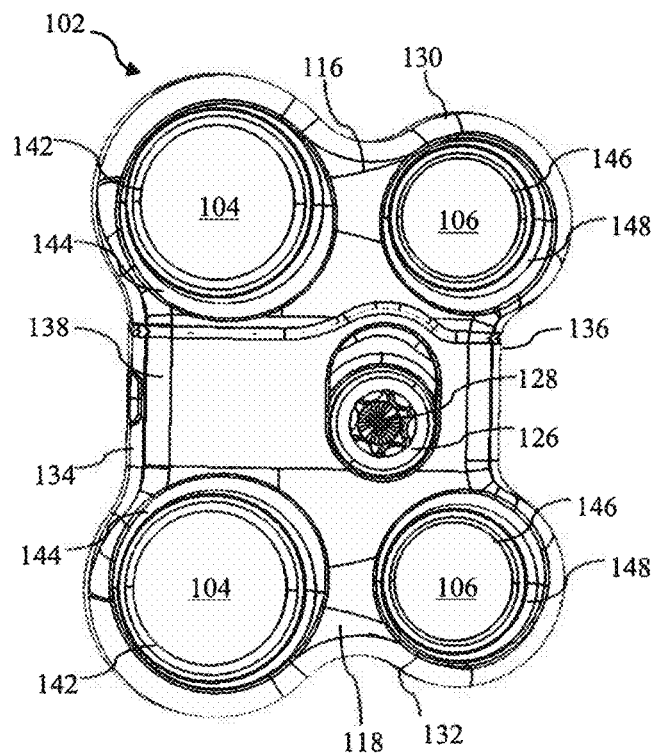
FIG. 3 is a front view of the base plate of the surgical fixation system of FIG. 1 in a closed configuration.

FIGS. 1-18 illustrate an example of a surgical fixation system 100 according to one embodiment of the present invention. With reference to FIGS. 1 and 2, the surgical fixation system 100 includes a base plate 102, a plurality of first bone anchors 104, a plurality of second bone anchors 106, and a translating locking element 108. The example shown herein is in the form of a base plate 102 configured for a single-level spinal fusion, and as such the base plate 102 is sized and configured to span a single intervertebral space while achieving purchase within each of the vertebral bodies adjacent the single intervertebral space. It is to be appreciated, however, the base plate 102 may be provided in any number of sizes to accommodate multiple-level spinal fusions without departing from the scope of the present invention, depending on the specific needs of the user. The base plate 102 may be provided in any shape suitable for spanning at least one intervertebral disc space without departing from the scope of the invention. The base plate 102 is particularly suitable for lateral insertion and placement against a lateral aspect of the vertebral bodies, however other uses are possible without departing from the scope of the present invention.

Figure 4:
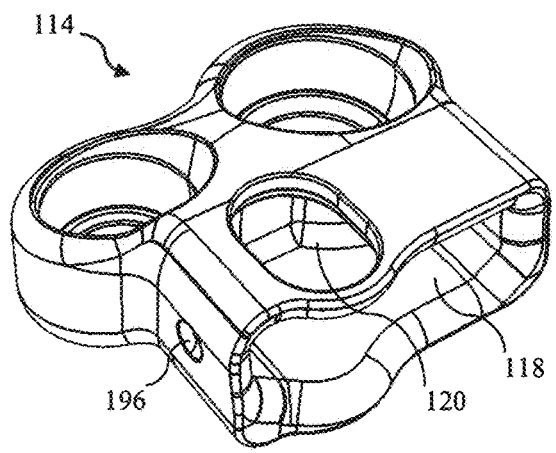
FIG. 4 is a perspective view of one component of the base plate of FIG. 3.
Figure 5:
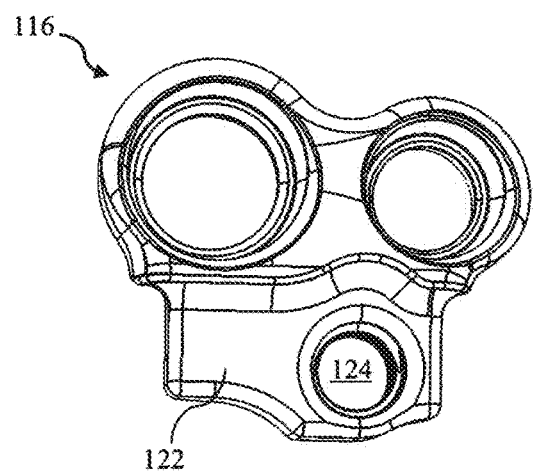
FIG. 5 is a front view of another component of the base plate of FIG. 3.

Referring to FIGS. 3-8, the base plate 102 will now be described in further detail. The base plate 102 has a female component 114 and a male component 116. The female component 114 comprises one first fixation aperture 110, one second fixation aperture 112, a receiving slot 118, and a lengthening slot 120 (FIG. 4). The male component 116 comprises one first fixation aperture 110, one second fixation aperture 112, an insertion portion 122, and a locking aperture 124 (FIG. 5). The insertion portion 122 of the male component 116 is sized and dimensioned to snugly fit within the receiving slot 118 of the female component 114. The male and female components 114,116 of the base plate 102 are securely mated to one another via translating locking element 108. According to one implementation, a set screw 126 (as shown with a hex tooling recess 128) is inserted through the lengthening slot 120 of the female component 114 and the locking aperture 134 of the male component 116 of the base plate 102, thereby creating a friction fit between the male and female components 114, 116 of the base plate 102.

Figure 37:
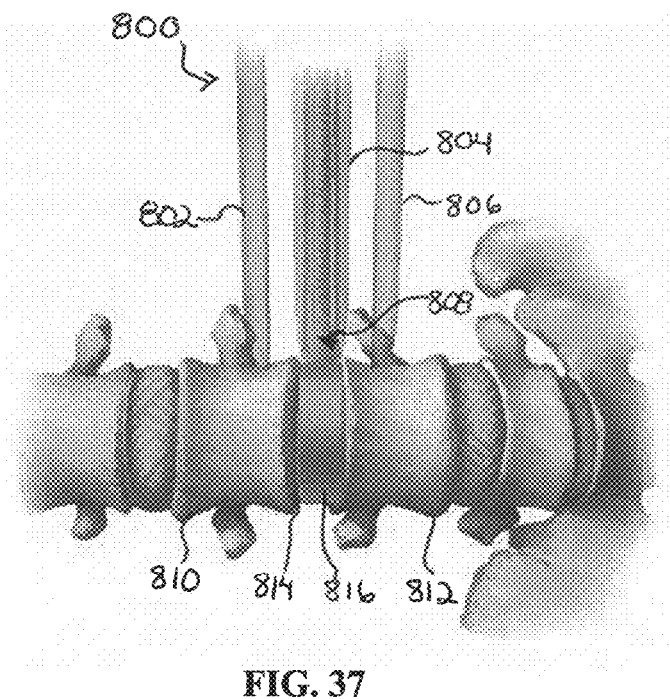
FIG. 37 is an anterior view of the spine with a surgical retraction system positioned via a lateral approach to the spine.

In its assembled state, the base plate 102 has a first end 130, a second end 132, a first side 134, and a second side 136. The base plate 102 further includes a first surface 138 and an opposing second surface 140. When properly positioned on a lateral aspect of a spinal column, the second surface 140 interfaces with the bone and thus is a vertebral contacting surface. Moreover, the first end 130 represents the cephalad-most (or top) end of the base plate 102, the first side 134 represents the posterior-most (or back) side of the base plate 102, and the second side 140 represents the anterior-most (or front) side of the base plate 102. First and second ends 130, 132 preferably each have a radius of curvature that is approximately equal to the radius of curvature of the retractor blades 802, 804, 806 (FIG. 37). This is significant for a number of reasons. Most importantly, having radii of curvature of the first and second ends 130, 132 approximately equal the radii of curvature of the retractor blades 802, 804, 806 enables the base plate 102 to be smoothly advanced along the operative corridor toward the surgical target site. This is a significant advantage when dealing with a minimally-invasive operative corridor in terms of operative time savings and avoiding disruption of the operative corridor.

The base plate 102 is provided with a pair of first fixation apertures 110 configured to receive at least a portion of the first bone anchors 104 therethrough, and a pair of second fixation apertures 112 configured to receive at least a portion of the second bone anchors 106 therethrough. The first fixation apertures 110 are provided by example as large circular holes, however the first fixation apertures 110 may be provided with any shape suitable for receiving at least a portion of the anchors 104 therethrough, including but not limited to ovoid or polygonal (e.g. rectangular, triangular, square, etc.) without departing from the scope of the present invention. The second fixation apertures 112 are provided by example as generally circular apertures, however the second fixation apertures 112 may be provided with any shape suitable for receiving at least a portion of the second fixation apertures 112 therethrough, including but not limited to ovoid or polygonal (e.g. rectangular, triangular, square, etc.). As will be explained in further detail below, the fixation apertures 110, 112 are located within the base plate 102 such that upon proper placement of the base plate 102 within a surgical target site, one of the first fixation apertures 110 and one of the second fixation apertures 112 are positioned over a first bone segment (e.g. a first vertebral body), and one of the first fixation apertures 110 and one of the second fixation apertures 112 are positioned over a second bone segment (e.g. a second vertebral body).

The first fixation apertures 110 are comprised of a first pocket 142 and a second pocket 144 and are sized and dimensioned to receive the first bone anchors 104 as will be described in detail below. The second fixation apertures 112 are shown and described herein as being circular holes. The second fixation apertures 112 have a first pocket 146 and a second pocket 146 and are sized and dimensioned to receive the second bone anchors 106 as will be described in detail below.

Figure 7:
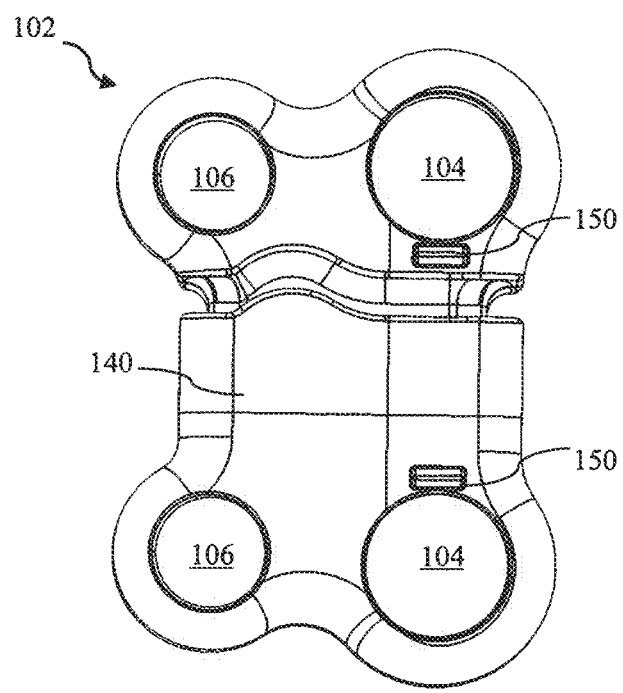
FIG. 7 is a back view of the base plate of the surgical fixation system of FIG. 1.
Figure 8:
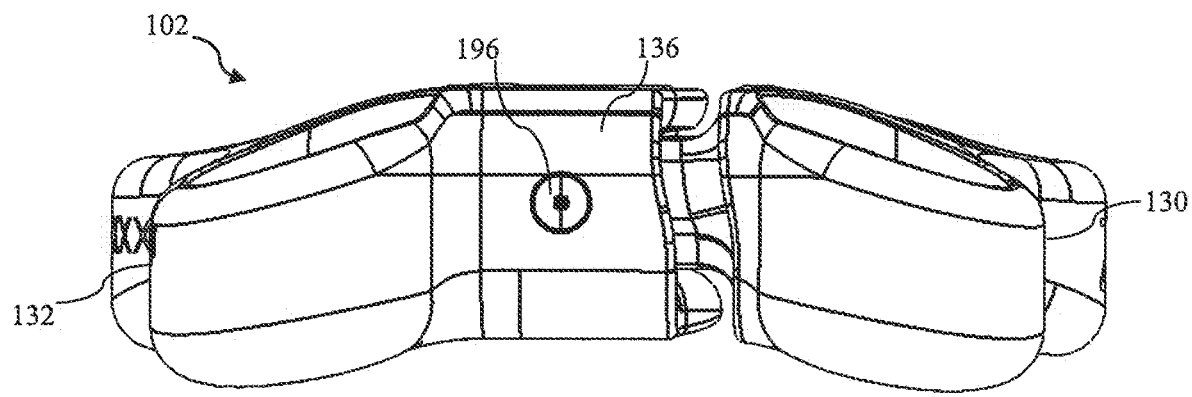
FIG. 8 is a side view of the base plate of the surgical fixation system of FIG. 1.
Figure 9:
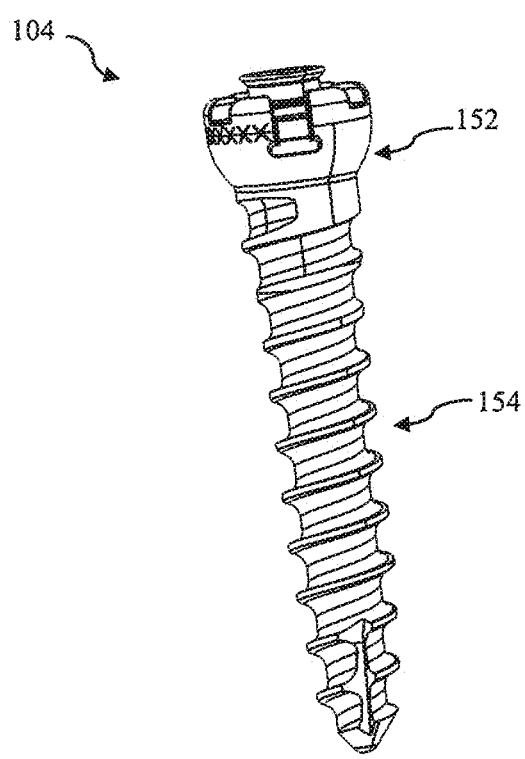
FIG. 9 is a perspective view of a first bone anchor of the surgical fixation system of FIG. 1.

As depicted in FIG. 7, the second surface 140 of the base plate 102 may include one or more protrusions 150 which engage the bones of the vertebral bodies, the disc space, or the vertebral spacer. This engagement prevents the base plate 102 from moving while the plurality of bone anchors 104, 106 are being placed. Base plate 102 may also have one or more engagement features 396 for engagement with an insertion device, for example translating plate inserter 818 as will be described in greater detail below. By way of example only, the tool engagement features may be located on the first side 134 (not shown) and second side 136 of the base plate 102 as shown in FIG. 8.

FIGS. 11-16 illustrate the first bone anchors 104 by way of example only in the form of threaded bone screws, however other forms of anchors are possible without departing from the scope of the present invention. The bone screw 104 each comprise a screw head 152 and a shank 154. The shank 154 includes threads 156 for threaded purchase into a bony segment (e.g. vertebral body).

Figure 10:
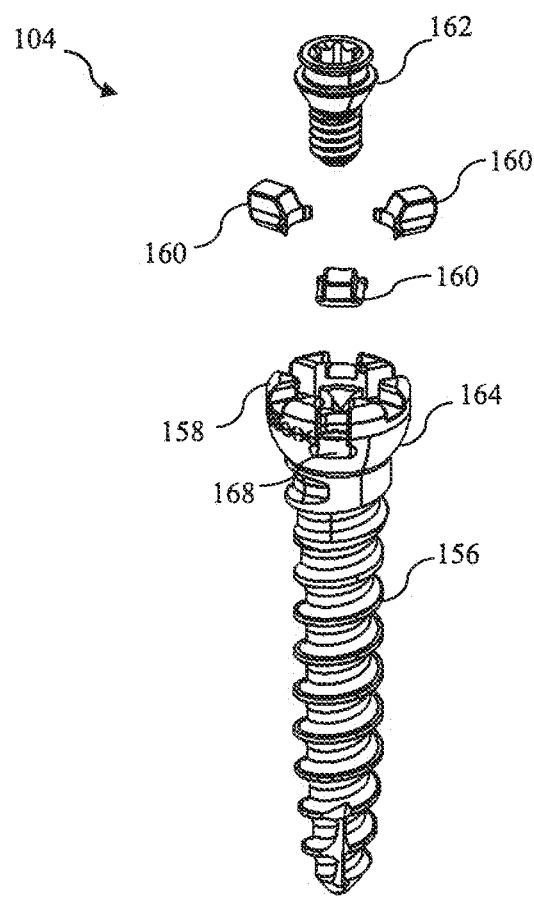
FIG. 10 is an exploded perspective view of the first bone anchor of FIG. 9.
Figure 11:
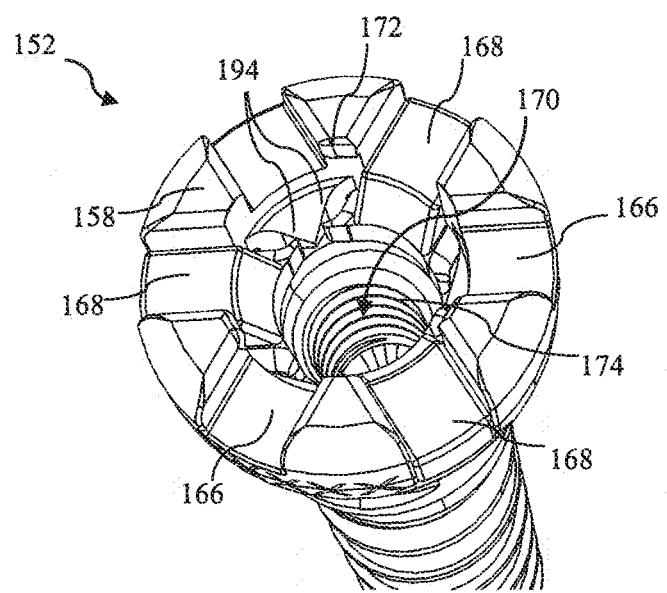
FIG. 11 is a partial perspective view of the screw head of the first bone anchor of FIG. 9.
Figure 12:
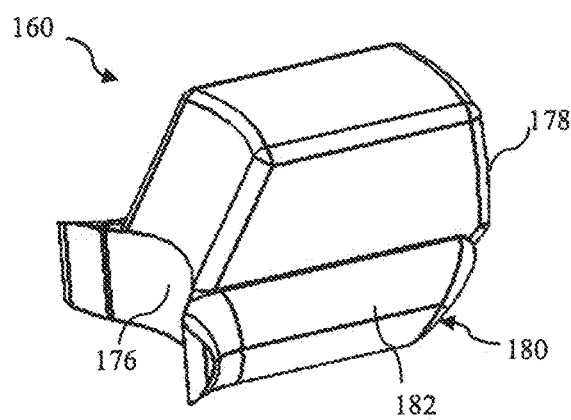
FIG. 12 is a perspective view of the lock of the first bone anchor of FIG. 9.
Figure 13:
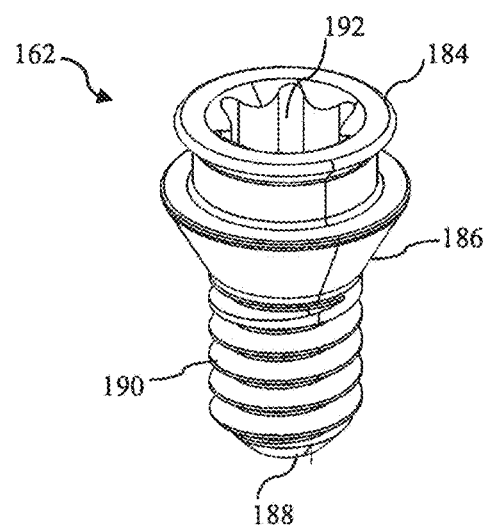
FIG. 13 is a perspective view of the lock screw of the first bone anchor of FIG. 9.

With reference to FIG. 10-11, the screw head 152 is comprised of an upper screw head region 158, a plurality of locks 160, a lock screw 162, and a bottom spherical portion 164. The upper screw head region 158 is includes of a plurality of cutouts 166 (which allow for screwdriver engagement as the bone screw 104 is driven into the bone as well as tightening the lock screw 162), a plurality of tracks (e.g. T-slot tracks 168), an interior chamber 170 (comprising internal threading 174), an undercut region 172, and wings 194. As depicted in FIG. 12, the plurality of locks 160 each include an inner lock face 176, an outer lock face 178 having a chamfered bottom surface 180, and a plurality of tabs 182. As FIG. 13 indicates, the lock screw 162 is preferably a conical screw with a proximal end 184, ramped portion 186, a distal end 188 with exterior threading 190, and an internal tool engaging recess 192. Preferably, the proximal end 184 has a larger diameter than the distal end 188 of the lock screw 362 which facilitates the use of a screw driver to retain the lock screw 362.

Figure 14:
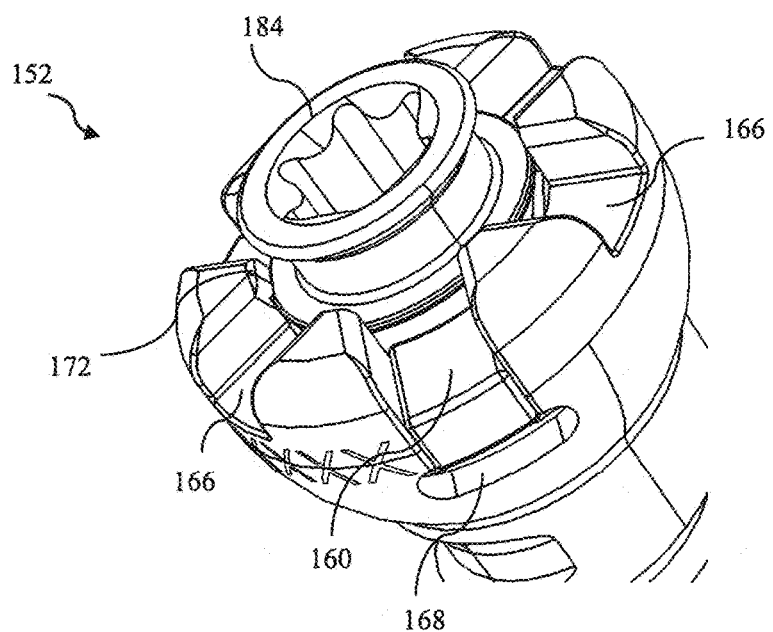
FIG. 14 is a partial perspective view of the first bone anchor of FIG. 9.
Figure 16:
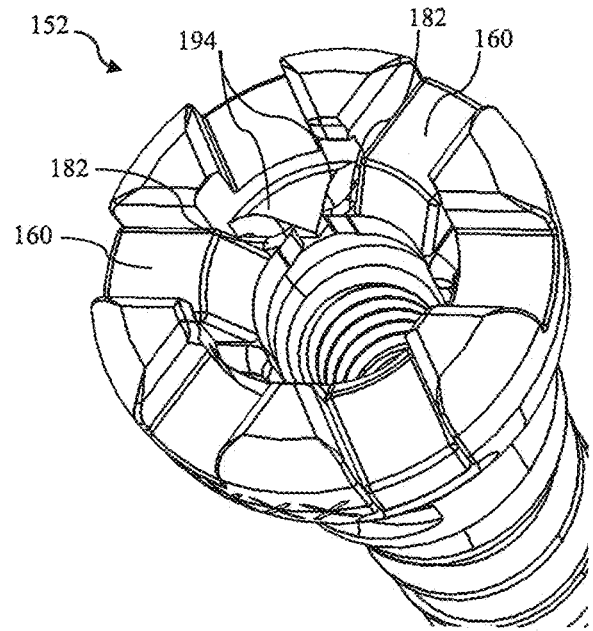
FIG. 16 is a partial perspective view showing the interaction between the locks and the screw head of the first bone anchor of FIG. 9.

As shown in FIG. 14, the locks 160 are contained inside the screw head 152 under the lock screw 162. The lock screw 162 is contained inside the screw head 152 under the undercut feature 172 on the interior of the screw head 170. During assembly, the lock screw 162 is threaded into the bone screw 104 via internal tool engaging recess 192. As the lock screw 162 is threaded, the undercut feature 172 splays outward to allow the lock screw 162 to pass. Once the lock screw 162 has passed, the undercut feature 172 returns to its initial position thereby containing the lock screw 162 inside the screw head 152. The locks 160 are contained inside the screw head 152 via tracks 168 which prevent the locks 160 from rotating, pivoting, or otherwise becoming displaced inside the screw head 152. The locks 160 are further constrained within the screw head 152 by tabs 188 on the locks 160 which abut one or more wings 194 inside the screw head 152, thereby preventing ejection of the locks 160 out of the screw head 152 as depicted in FIG. 16.

The surgical fixation system 100 also includes a locking mechanism for fixedly coupling bone anchors 104 to the base plate 102 after implantation. According to one embodiment, fixation apertures 110 each have a first spherical pocket 142 and a second spherical pocket 144 sized and dimensioned for receiving a bone screw 104 therein. The bone screw 104 is placed through the base plate 102 and mates with the first spherical pocket 142 within the base plate 102 via the matching bottom spherical surface 164 of the screw head 152. The bone screw 104 has a cone of angulations in which it can be placed and still lock to the plate 102. By way of example only, the cone of angulations may be within a range between 0 and 10 degrees. Locks 160 have a spherical inner face 170 which fit into the second spherical pocket 144. Once the bone screw 104 is fully seated with the bottom spherical surface 164 of the screw head 152 within the first spherical pocket 142, a screw driver may rotate the lock screw 162 via the inner tool engaging recess 192 towards the interior of the screw head 170. As this happens, the ramp 186 of the lock screw 162 slides along the internal lock face 176 to push the lock 160 radially outward.

Figure 15:
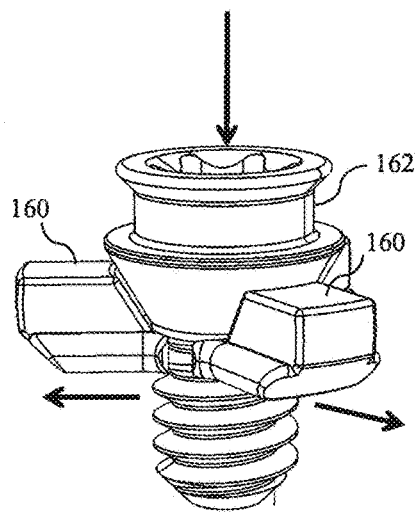
FIG. 15 is a perspective view showing the interaction between the locks and the lock screw of the first bone anchor of FIG. 9.

When the distal end 188 of the lock screw 162 threads into the interior of the screw head 172 via the exterior threading 190, the tabs 182 of the lock 160 expand radially outward, causing them to lock the bone screw 104 to the base plate 102 (as depicted in FIG. 15). With the locks 160 fully engaged in this manner, further polyaxial motion of the bone screw 104 is prevented as is unwanted backout of the bone screw 104. If the lock 160 is in an extended position during screw insertion, the chamfered bottom 180 of the outer lock face 178 may guide the lock 160 back into the screw head 152 if necessary. It is to be appreciated that in the pockets 142, 144 are spherical in this embodiment, they may be any shape including cylindrical, flat, etc. Furthermore, the outer lock face 178 is spherical in this embodiment, it may be any shape including, but not limited to, spherical, cylindrical, flat, etc. While the locking mechanism was explained above with respect to bone screw 104, it is to be appreciated that the locking mechanism may also be utilized with respect to a second bone anchor 106.

Figure 17:
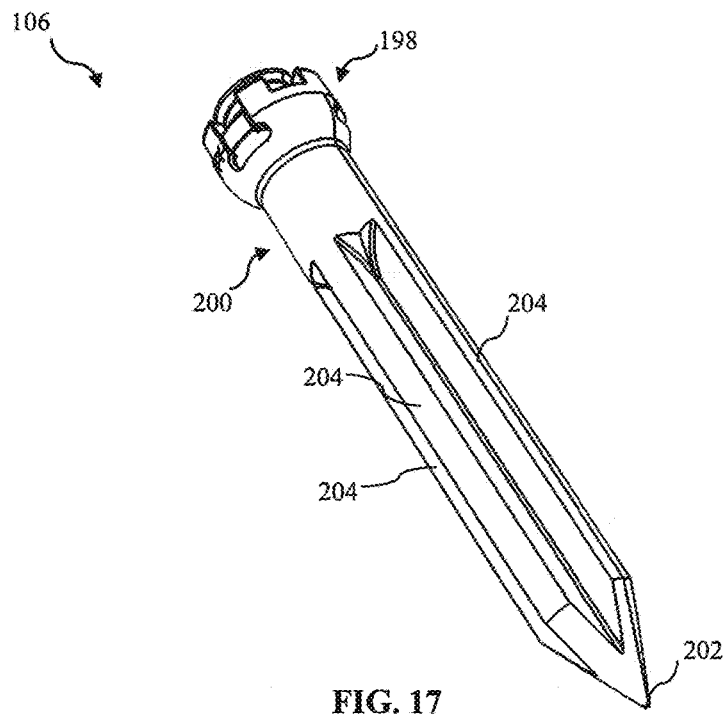
FIG. 17 is a perspective view of a second bone anchor of the surgical fixation system of FIG. 1.

FIG. 17 illustrates the second bone anchors 106 by way of example only in the form of bone staples, however other forms of anchors are possible without departing from the scope of the present invention. The bone staple 106 comprises a staple head 198 and an elongate body 200. The elongate body 200 preferably includes a pointed distal tip 202 for purchase into a bony segment (e.g., vertebral body). Bone staple 106 differs from the threaded bone screw 104 in that the bone staple 106 does not have threads but rather blades 204 that run down the length of the elongate body 200. The flat faces of the blades 204 (shown here by way of example only, in a cruciform configuration) prevent rotation of the bone staple 106 about its central axis. Because the bone staple 106 is not threaded, it can be impacted into the bone quickly, thereby reducing the time required for implantation. The staple head 198 is mated and locked to the plate 102 via first and second spherical pockets 146, 148 the same way as described above for the bone screw 104 and a discussion of the locking mechanism will not be repeated here.

Figure 6:
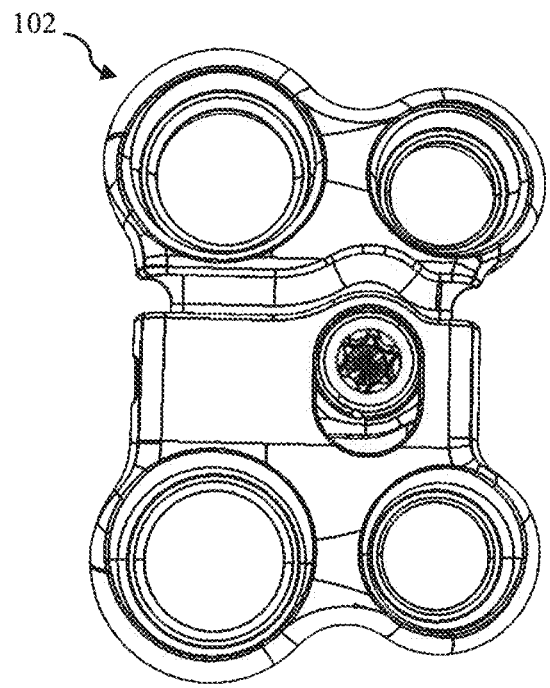
FIG. 6 is a front view of the base plate of FIG. 3 in an open configuration.

In minimally invasive lateral approaches to the spine, base plates 102 of shorter lengths (defined as the distance between first end 130 and second end 132) facilitate the ease of insertion into and through the surgical corridor. However, depending on patient's anatomy and/or surgical requirements, base plates 102 of longer lengths may be advantageous notwithstanding the difficulties associated with inserting a longer plate. In a preferred embodiment of the present invention, the base plate 102 of the surgical fixation system 100 contains an in situ lengthening feature (translating locking element 108) that allows the length of the base plate 102 to be variably lengthened in situ. Referring back now to FIG. 3, the base plate 102 is shown in its shortest length configuration (i.e., a closed position). In the closed position, the male portion 116 of the base plate 102 is fully inserted into the female portion 114 such that the set screw 126 is maximally situated within the lengthening slot 120. Referring now to FIG. 6, the base plate 102 is shown in its longest length configuration (i.e., an open position). In the open position, the male insertion portion 122 is extended away from the female receiving slot 118 such that at least some portion of the male insertion portion 122 is not contained within the female receiving slot 118. This distance of such a non-contained portion is limited by the distance between the two ends of the lengthening slot 120 within the translating locking element 108. This distance can be any anatomically-appropriate distance, for example, somewhere within a range between 0.1 mm and 5 mm, for example 2 mm. In the open position, the set screw 126 is minimally situated within the lengthening slot 120.

In a preferred embodiment, the base plate 102 is inserted in its smallest, closed configuration via a lateral approach to lateral aspect of the spine. Once the base plate 102 has reached the spinal target site, the plate 102 may be lengthened until the set screw 126 prevents any further extension within the lengthening slot 120. However, it is to be appreciated that the base plate 102 may be lengthened any distance allowed by the translating locking element 1308 based upon patient anatomy and surgical requirements. Once the desired length has been achieved, the translating locking element 108 may be secured, thereby locking the length into position. To do this, the set screw 126 may be driven down, via tooling recess 128 as shown in FIG. 18. As the set screw 126 is driven down, the threads (not shown) on the locking aperture 124 of the male component 116 push against one another. Once the set screw 126 is fully advanced, it drives the top of the male component 116 upwards towards the top of the female component 114, thereby locking the base plate 102 into the desired length. Additionally, the engagement surfaces on the male component 116 and female component 114 may be textured to increase the friction between the two when the base plate 102 is locked into its final configuration.

The base plate 102, anchors 104, 106, and/or locking components 160, 162, etc. may be formed of any material suitable to provide rigid fixation between two bony segments. By way of example, all may be formed of a biocompatible metal, such as titanium. The base plate 102 may be provided with any size necessary to complete the desired spinal fixation.

FIGS. 19-20 illustrate a second embodiment of the surgical fixation system 300. The surgical fixation system 300 is similar to surgical fixation system 100 except that it has threaded bone staples 302 instead of unthreaded bone staples. Threaded bone staple 302 (FIG. 20) comprises a staple head 304 and an elongate body 306. The elongate body 306 includes threads 308 for threaded purchase into a bony segment (e.g. vertebral body). The threaded bone staple 306 is mated and locked to the plate the same way as described above for the bone screw 104. It is to be appreciated that surgical fixation system 300 includes all other components and features of surgical fixation system 100 such that a discussion of those components and features will not be repeated here.

Figure 21:
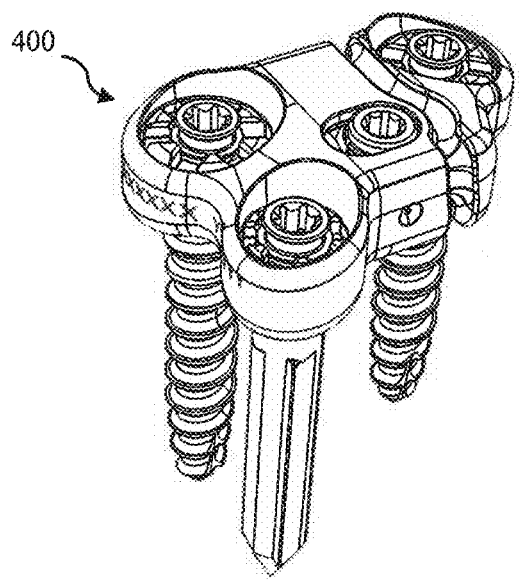
FIG. 21 is an example of a surgical fixation system according to a third embodiment of the present invention.

FIG. 21 illustrates a third embodiment of the surgical fixation system 400. The surgical fixation system 400 is similar to surgical fixation system 100 except that it has a pair of first fixation apertures 110 for receiving a pair of first bone anchors 104 and a singular fixation aperture 112 for receiving one bone anchor 106 (e.g. bone staple 106). It is to be appreciated that surgical fixation system 400 includes all other components and features of surgical fixation system 100 such that a discussion of those components and features will not be repeated here.

Figure 22:
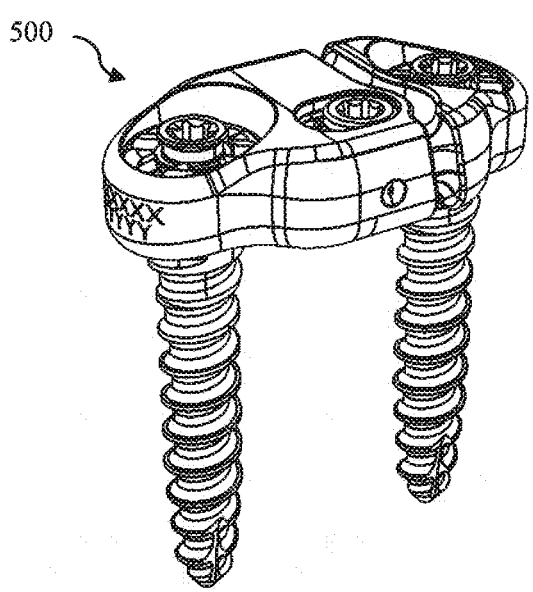
FIG. 22 is an example of a surgical fixation system according to a fourth embodiment of the present invention.

FIG. 22 illustrates a fourth embodiment of the surgical fixation system 500. The surgical fixation system 500 is similar to surgical fixation system 100 except that it does not include second fixation apertures 112 and thus does not receive bone anchors 106. It is to be appreciated that surgical fixation system 500 includes all other components and features of surgical fixation system 100 such that a discussion of those components and features will not be repeated here.

Figure 23:
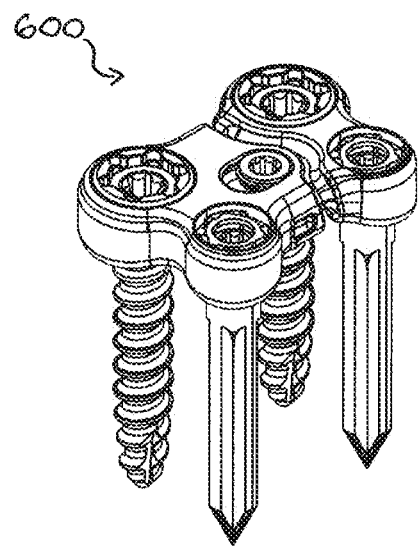
FIG. 23 is an example of a surgical fixation system according to a fifth embodiment of the present invention.
Figure 24:
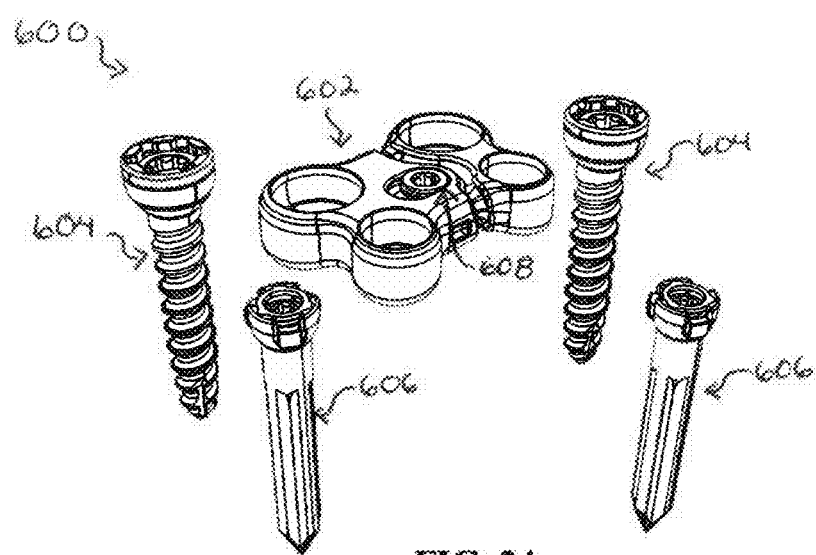
FIG. 24 is an exploded view of the surgical fixation system of FIG. 23.

FIGS. 23-35 illustrate a fifth embodiment of the surgical fixation system 600. With reference to FIGS. 23 and 24, the surgical fixation system 600 includes a base plate 602, a plurality of first bone anchors 604, a plurality of second bone anchors 606, and a translating locking element 608. The example shown herein is in the form of a base plate 602 configured for a single-level spinal fusion, and as such the base plate 602 is sized and configured to span a single intervertebral space while achieving purchase within each of the vertebral bodies adjacent the single intervertebral space. It is to be appreciated, however, the base plate 602 may be provided in any number of sizes to accommodate multiple-level spinal fusions without departing from the scope of the present invention, depending on the specific needs of the user. The base plate 602 may be provided in any shape suitable for spanning at least one intervertebral disc space without departing from the scope of the invention. The base plate 602 is particularly suitable for lateral insertion and placement against a lateral aspect of the vertebral bodies, however other uses are possible without departing from the scope of the present invention. It is to be appreciated that the base plate 602 includes all components and features of the base plate 102 such that a discussion of those components and features will not be repeated here.

The first bone anchors 604 are shown and described herein by way of example only (FIGS. 25-29), in the form of threaded bone screws, however other forms of anchors are possible without departing from the scope of the present invention. The bone screws 604 each comprise a head region 648 and a shank 650. The shank 650 includes threads 652 for threaded purchase into a bony segment (e.g. vertebral body).

Figure 25:
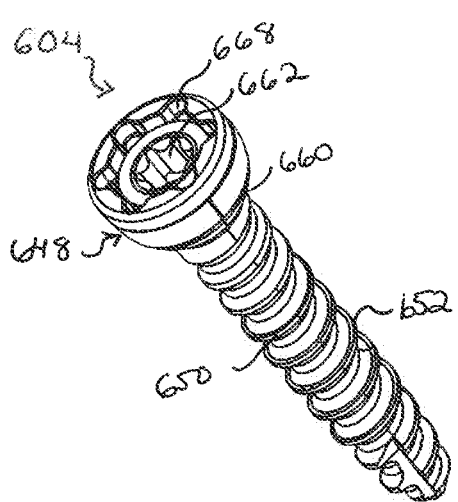
FIG. 25 is a perspective view of a first bone anchor of the surgical fixation system of FIG. 23.
Figure 26:
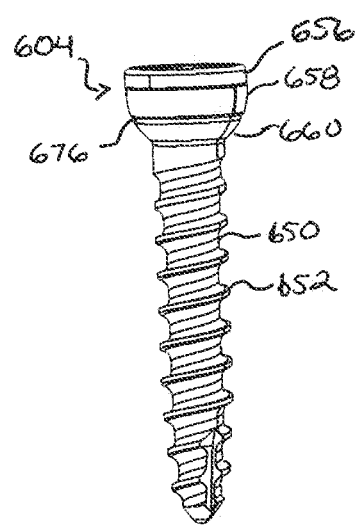
FIG. 26 is front view of the first bone anchor of FIG. 25.
Figure 27:
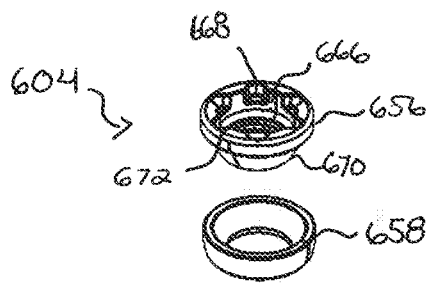
FIG. 27 is an exploded view of the first bone anchor of FIG. 25
Figure 27:
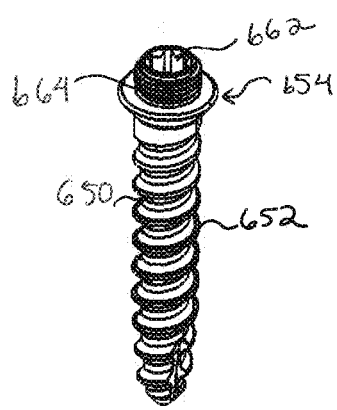
Figure 28:
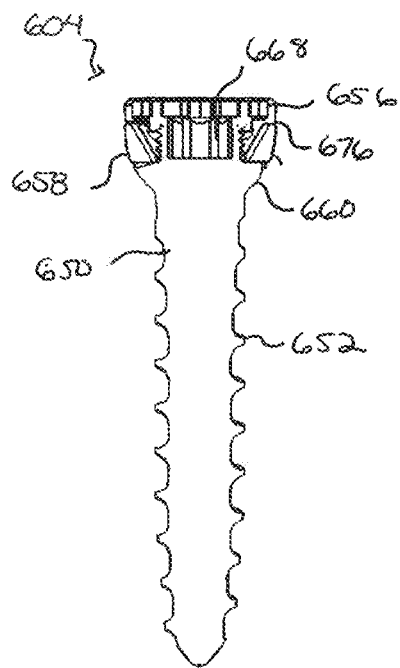
FIG. 28 is a cross-sectional view of the first bone anchor of FIG. 25.
Figure 29:
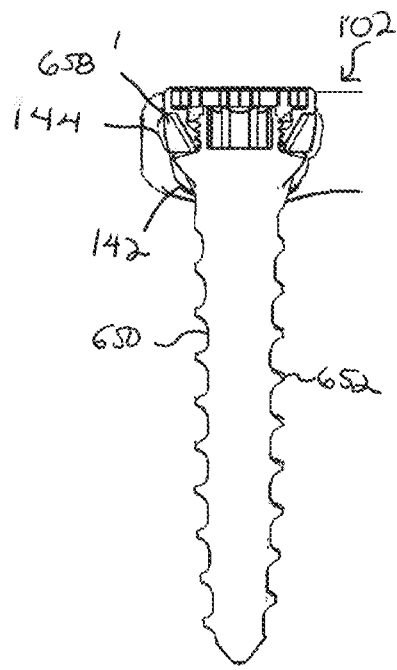
FIG. 29 is a cross-sectional view of the first bone anchor situated in the base plate of the surgical fixation system of FIG. 23.

The head region 648 is comprised of a screw head 654, a screw cap 656, a washer 658 (preferably a split-ring washer), and a bottom spherical surface 660. The screw head 654 is further comprised of an inner tool engaging recess 662 for engaging with a tool capable of driving the screw into bone (e.g. a hex recess as shown in FIG. 25) and an exterior thread 664. The cap 656 is further comprised of an open proximal end 666, an outer tooling recess 668 capable of driving the screw cap 656 in towards the spherical bottom surface 660 of the head 654, a tapered distal end 670, and internal threading 672 disposed within the inner aperture 674 (which preferably extends from just below the outer tooling recess 668 all the way to the tapered distal end 670).

The cap 656 is sized and dimensioned to be positioned through the split ring washer 658 and at least partially threadably advanced within the external threading 664 on the screw head 654. Between the top of the cap 656 and the washer 658, there is a circumferential recess 676. Within this recess, the washer 658 is freely able to spin around the screw head 654 and move between the top and bottom surfaces of the screw head 654.

The bone screw 604 is placed through the base plate 602 and mates with a first spherical pocket 642 within the base plate 602. The bone screw 604 has a cone of angulations in which it can be placed and still lock to the plate 602. By way of example only, the cone of angulations may be within a range between 0 and 10 degrees. Once the bone screw 604 is fully seated with the bottom spherical surface 660 of the screw head 654 within a first spherical pocket, a driver mechanism may rotate the screw cap 656 via the outer tooling recess 668 such that the screw cap 664 is advanced towards the bottom spherical surface of the screw head 654. As this happens, the screw cap 656 compresses the split ring washer 658 and forces the washer 658 radially outward into a second spherical pocket 644 in the base plate 602. The force of the split ring washer 658 on the base plate 602 prevents the first bone anchor 604 from rotating or backing out. With the bone screw 604 fully positioned within the first fixation aperture 610, the bone screw 604 is prevented from rotating about its axis, rotating about its head 654, and translating within the aperture 610.

Figure 30:
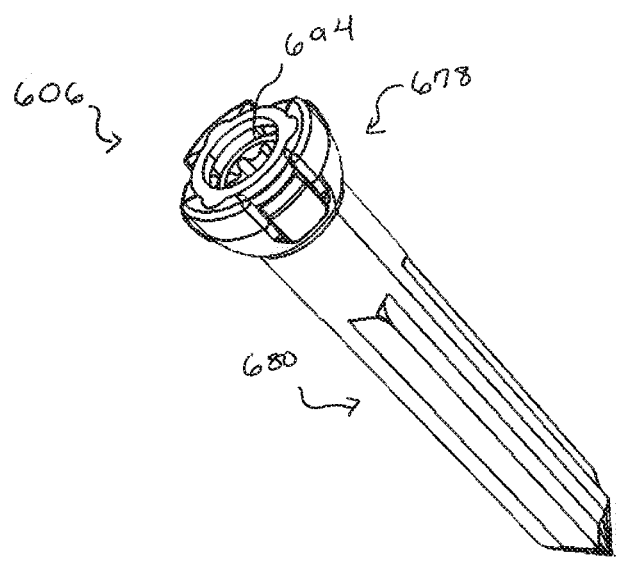
FIG. 30 is a perspective view of a second bone anchor of the surgical fixation system of FIG. 23.
Figure 31:
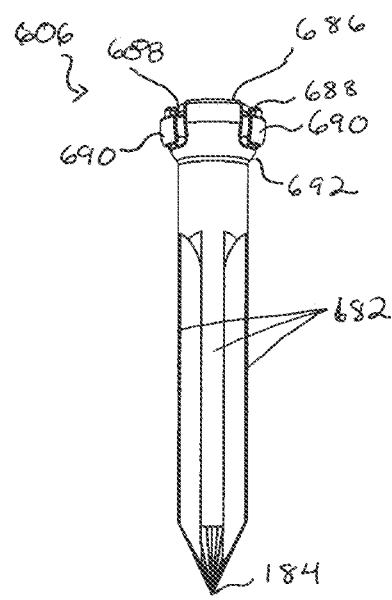
FIG. 31 is a front view of the second bone anchor of FIG. 30.

The second bone anchors 606 are shown and described herein by way of example only, in the form of a bone staple in FIGS. 30-35, however other forms of anchors are possible without departing from the scope of the present invention. A bone staple 606 may provide the advantages of being smaller, faster to insert, and the ability to resist rotation as compared to threaded bone screws (e.g., threaded bone screws 604). As depicted in FIGS. 30-31, the bone staples 606 each comprise a head region 678 and an elongated shaft 680. The elongated shaft 680 comprises a plurality of orthogonally-disposed fins 682 and a pointed distal tip 684 designed for purchase within a bony segment (e.g. a vertebral body).

Figure 32:
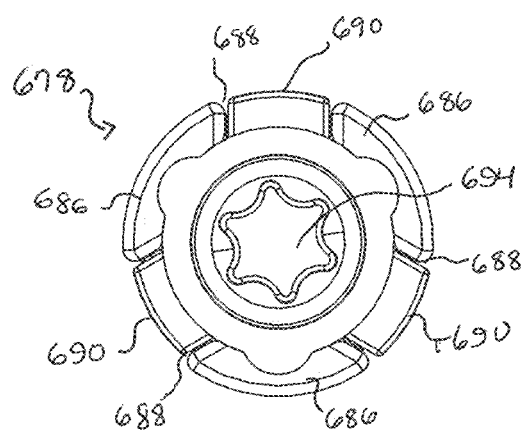
FIG. 32 is a top view of the second bone anchor of FIG. 30 in a first configuration.
Figure 33:
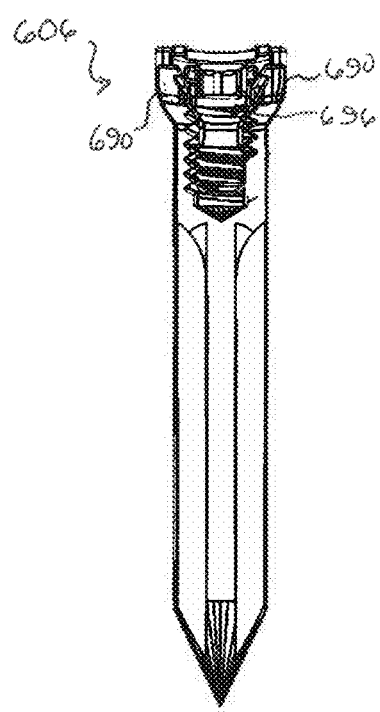
FIG. 33 is a cross-sectional view of the second bone anchor of FIG. 30 in the first configuration.
Figure 34:
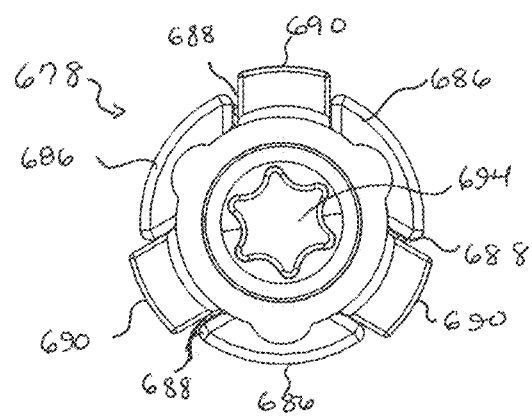
FIG. 34 is a top view of the second bone anchor of FIG. 30 in a second configuration.
Figure 35:
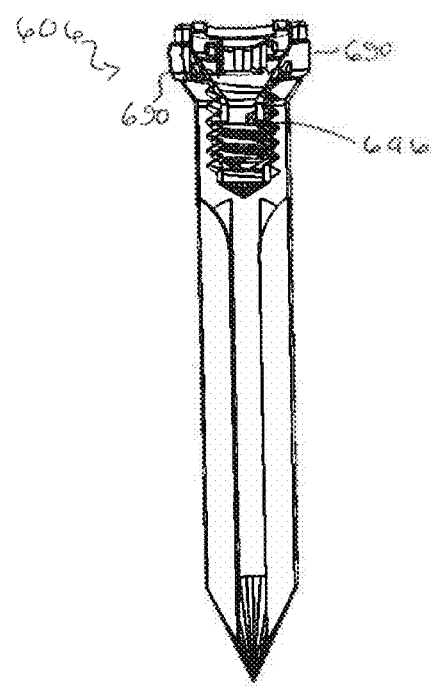
FIG. 35 is a cross-sectional view of the second bone anchor of FIG. 30 in the second configuration.
Figure 36:
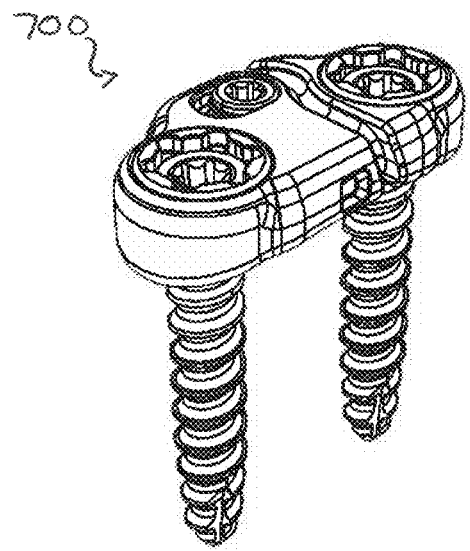
FIG. 36 is an example of the surgical fixation system according to a sixth embodiment of the present invention.

The head region 678 is comprised of an upper head portion 686 with a plurality of cutouts 688, a plurality of independent tabs 690 extending through the cutouts 688, and a bottom spherical surface 692 (FIGS. 32-33). The upper head portion 686 is further comprised of an inner tool engaging recess 694 disposed on the top of the head 678, which may be a hex recess as shown in FIG. 30. The bone staple 606 is placed through the base plate 602 and mates with a spherical pocket within the base plate 602. The bone staple 606 has a cone of angulations in which it can be placed and still lock to the plate 602. By way of example only, the cone of angulations may be within a range between 0 and 10 degrees. Once the bone screw 606 is fully seated with the bottom spherical surface 692 of the upper head portion 686 within the spherical pocket, a driver mechanism forces a conical screw 696 disposed within the head region 678 down into the bone staple 606. As this happens, the conical screw 696 deforms the tabs 690 radially outward towards the base plate 602 (FIGS. 34-35). The force of the tabs 690 on the base plate 602 prevents the bone staple 606 from rotating or backing out.

In minimally invasive lateral approaches to the spine, base plates 602 of shorter lengths (defined as the distance between first end 630 and second end 632) facilitate the ease of insertion into and through the surgical corridor. However, depending on patient's anatomy and/or surgical requirements, base plates 602 of longer lengths may be advantageous notwithstanding the difficulties associated with inserting a longer plate. In a preferred embodiment of the present invention, the base plate 602 of the surgical fixation system 600 contains an in situ lengthening feature that may be the same as discussed above with relation to the translating locking element 108. As such, this feature will not be repeated here.

FIG. 32 illustrates a sixth embodiment of the surgical fixation system 700. The surgical fixation system 700 is similar to surgical fixation system 600 except that it does not include second fixation apertures 612 and thus does not receive bone anchors 606. It is to be appreciated that surgical fixation system 700 includes all other components and features of surgical fixation system 600 such that a discussion of those components and features will not be repeated here.

Although shown and described above as assembled in space, the surgical fixation systems of the present invention are assembled in situ during a surgical procedure. One such example is a spinal fusion surgery. The surgical fixation systems disclosed herein are optimally used in a direct lateral surgical procedure in which the spine is approached laterally at approximately a 90° angle relative to the patient's spine. The first step in such a procedure is to create an operative corridor through the patient's skin and underlying musculature to the spinal target site, for example, a symptomatic intervertebral disc located between first and second adjacent vertebral bodies. The specific technique involved in performing this step is shown and described in commonly-owned U.S. Pat. No. 7,905,840, filed on Oct. 18, 2004, patented on Mar. 15, 2011, and entitled "Surgical Access System and Related Methods," the entire contents of which are hereby incorporated by reference into this disclosure as if set forth fully herein.

A key component of the technique of establishing the operative corridor is the surgical retraction system 800 (FIG. 37). Notably, the surgical retraction system 800 includes a plurality of retractor blades 802, 804, 806. The surgical retraction system 800 is introduced into the surgical target site in an initial "closed" position wherein the retractor blades 802, 804, 806 together form a generally cylindrical tubular member. Thereafter, the surgical retraction system 800 is moved to an "open" position in which the retractor 802, 804, 806 are spread apart from one another, thereby establishing the operative corridor to the surgical target site. As the three blades 802, 804, 806 initially form a generally cylindrical tubular member in a closed position, each blade has a defined radius of curvature. This radius of curvature is approximately equal to the radius of curvature of the first and second ends 130, 132 of the base plate 102 as discussed above.

After establishment of the operative corridor to the surgical target site, the next step is to perform the necessary therapeutic technique to relieve the distress on the target disc space. For example, this may involve performing a partial or total discectomy (removing damaged or degenerative disc tissue from the intervertebral space) and then inserting a spinal fusion implant such as a bone graft (e.g., allograft, autograft, or xenograft) or synthetic fusion cage (e.g., titanium and/or PEEK) into the space. One example of a synthetic spinal fusion implant that may be used is shown and described in commonly-owned U.S. Pat. No. 7,819,891 filed on Mar. 29, 2005, issued on Apr. 5, 2011, and entitled "Systems and Methods for Spinal Fusion," the entire contents of which are hereby incorporated by reference into this disclosure as if set forth fully herein. These spinal fusion implants (natural or synthetic) may be used with or without additional fusion-inducing materials, such as an orthopedic matrix containing, for example, calcium hydroxyapatite, bone morphogenic protein (BMP), demineralized bone matrix, collagen bone graft matrix, and stem cell material, or other fusion-promoting substances placed within the spaces of the implant, while the implant is advanced into the intervertebral space.

Referring to FIG. 37, a surgical target site 808 is shown comprising a first vertebral body 810, a second vertebral body 812, and an intervertebral disc space 814 situated between the first and second vertebral bodies 810, 812. A spinal fusion implant 816 has been inserted into the disc space 814. With the distressed disc space addressed, the next step is to add supplemental fixation, if desired.

In this case, the surgical fixation system 100 of the present invention is implanted through the operative corridor within the surgical target site 808 to help with the fusion process. While the steps of implanting the surgical fixation system is described herein with respect to surgical fixation system 100, it is to be appreciated that surgical fixation systems 300, 400, 500, 600, and 700 may also be implanted in a similar manner.

The first step in implanting the surgical fixation system 100 is to implant an appropriately-sized bone plate 102 over the first and second vertebral bodies 810, 812. According to one implementation, the size of the base plate 102 relates to its size in the open position and corresponds to the size of the spinal fusion implant 816. This allows for insertion of the base plate 102 in its closed position through the surgical retraction system 800 and expansion into its open position (via translating locking mechanism 108) at the surgical target site 808.

Figure 38:
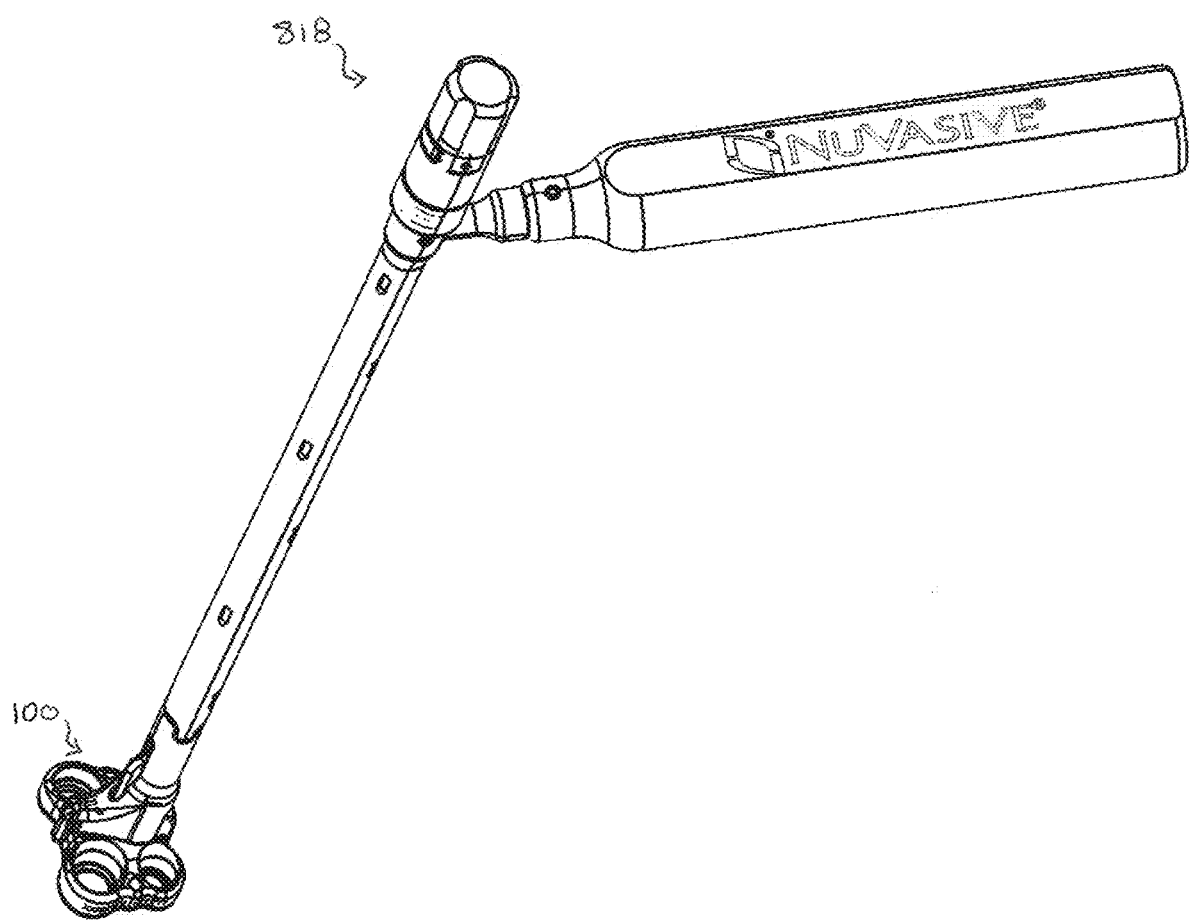
FIG. 38 is a perspective view of the base plate of FIG. 1 coupled to an example of a plate inserter according to one embodiment.
Figure 39:
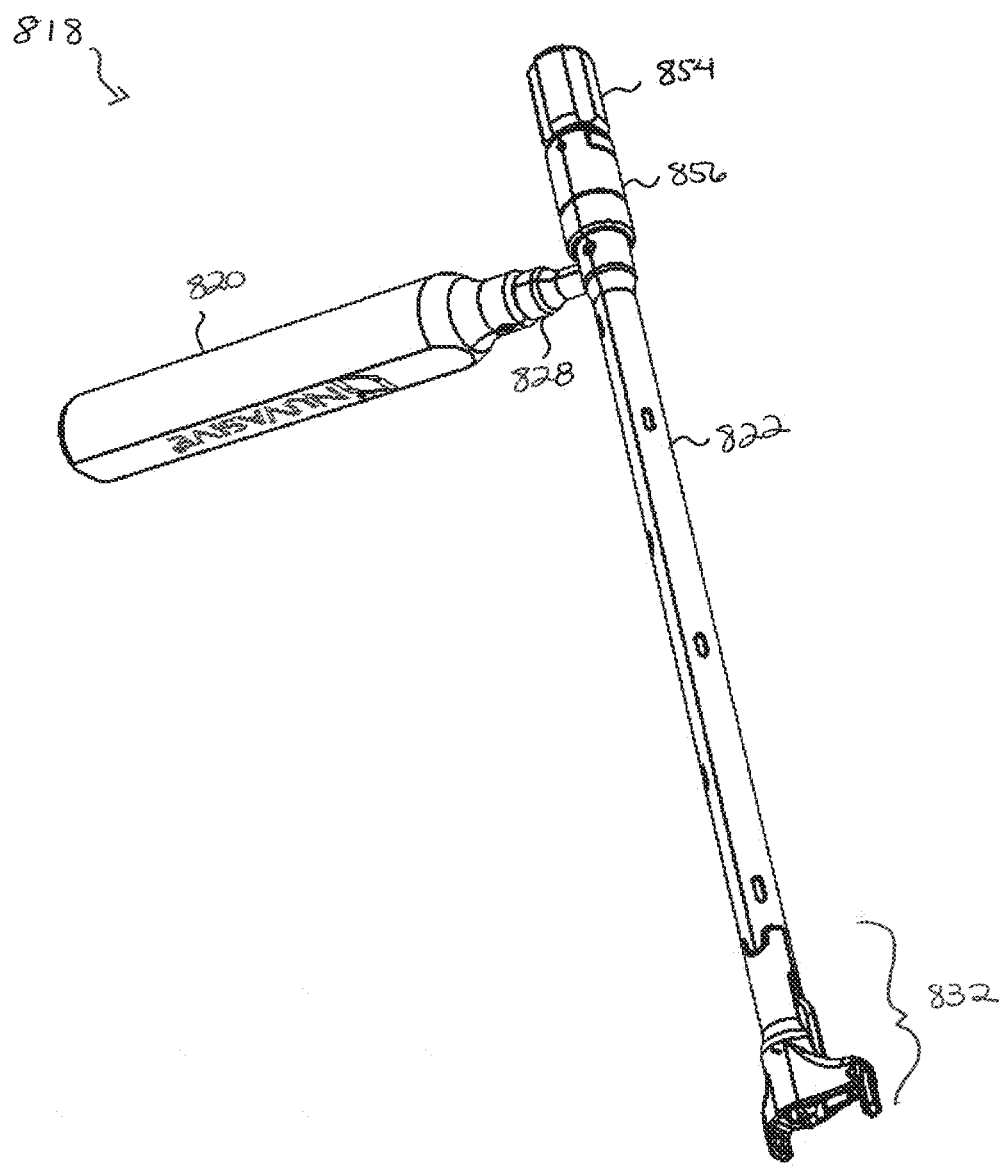
FIG. 39 is a perspective view of the plate inserter of FIG. 38.
Figure 40:
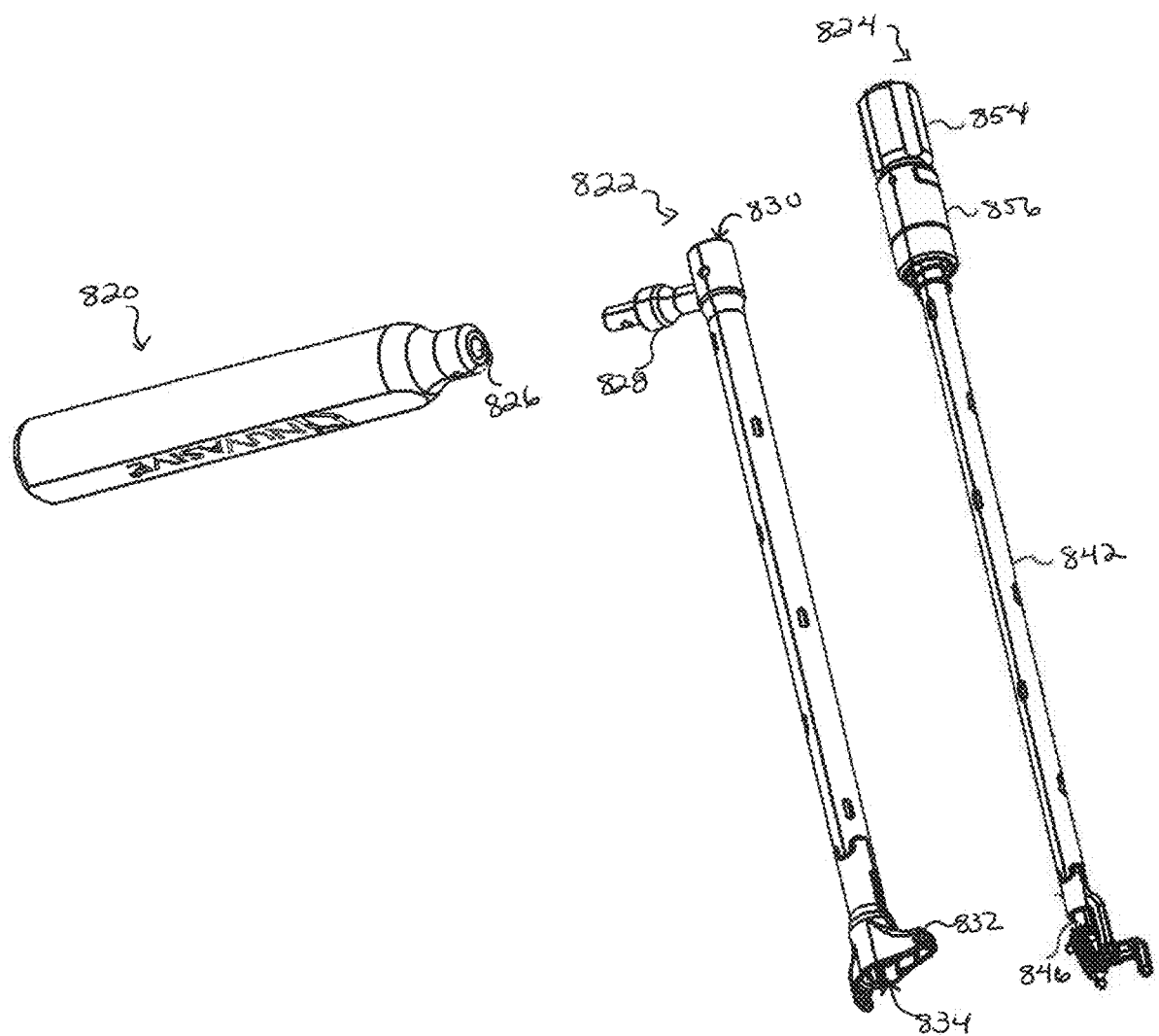
FIG. 40 is an exploded view of the plate inserter of FIG. 38.
Figure 41:
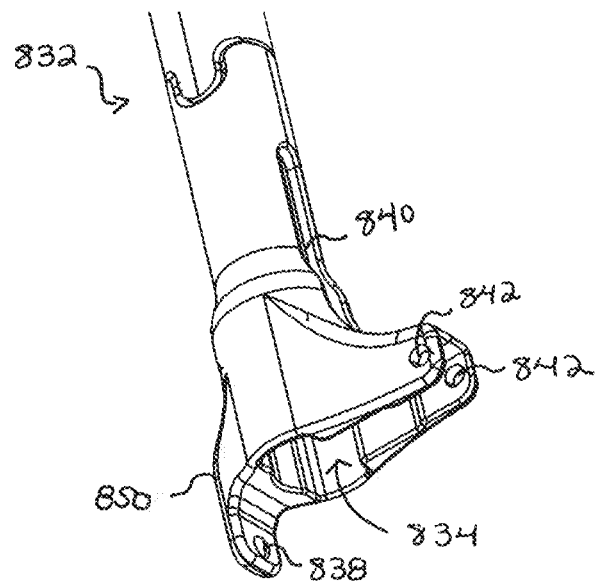
FIG. 41 is a partial perspective view of the distal insertion head of the plate inserter of FIG. 37.

As described in FIGS. 38-48, there is also provided a plate inserter 818 for inserting the surgical fixation system 100, preferably from a lateral approach. The plate inserter 818 is comprised of a handle 820, an elongate tubular element 822, and an insertion and translation assembly 824, as illustrated in FIGS. 38-39.

The handle 820 is generally disposed near the proximal end of the plate inserter 818. The handle may be further equipped with a universal connector feature 826 to allow for ease of attachment with the elongate tubular element 822 via handle adapter 828.

Figure 42:
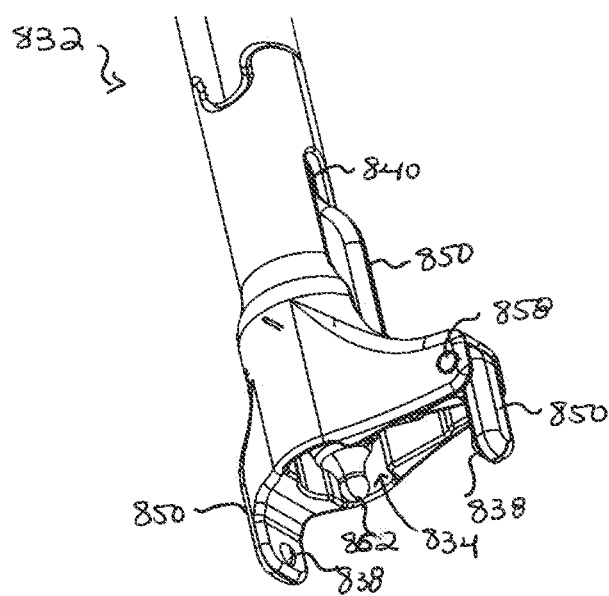
FIG. 42 is a partial perspective view of the distal portion of the plate inserter of FIG. 37.

The elongate tubular element 822 includes a handle adapter 828, an inner bore 830, and a distal insertion head 832. The handle adapter 828 is removeably coupled to the handle 820 via the universal connector feature 826. The inner bore 830 extends from the proximal to the distal ends of the elongate tubular element 820 and is dimensioned to receive the outer shaft 844 and the inner shaft 846 of the insertion and translation assembly 824. As best viewed in FIG. 41, the distal insertion head 832 is comprised of a central opening 834, a fixed gripping arm 836 with a plate engagement feature 838, a lateral slot 840, and a plurality of pin-receiving apertures 842 for receiving one or more pivot pins 858. The central opening 834 of the distal insertion head 832 extends distally from the inner bore 830 of the elongate tubular element 822. The central opening 834 houses one or more components of the insertion and translation assembly 824 including the outer shaft 844, the inner shaft 846, the pivoting gripping arm 850, and the pivoting lever 852 which is shown in FIG. 42 and as will be described in greater detail below.

The elongate tubular element 822 is dimensioned to receive a spring (not shown) and one or more actuating knobs 854, 856 comprising part of the insertion and translation assembly 826 at its proximal end. The elongate tubular element 822 is generally cylindrical and of sufficient length to allow the plate inserter 818 to span from the surgical target site to a location sufficiently outside of the patient's body so the handle 820 and actuating knobs 854, 856 can be easily accessed by the surgeon or a complimentary controlling device.

The insertion and translation assembly 824 is comprised of outer shaft 844, an inner shaft 846 disposed within the central lumen 848 of the outer shaft, a pivoting gripping arm 850 having at least one pivoting linkage and a plate engagement feature 838, a pivoting lever 852, a first actuating knob 854 for actuating the pivoting gripping arm 850, and a second actuating knob 856 for actuating the pivoting lever 852. At least a portion of the insertion and translation assembly 824 extend into the central opening 834 of the distal insertion head 832.

The pivoting gripping arm 850 is housed within the distal insertion head 832 at least partially through the lateral slot 840. The lateral slot 840 is sized and dimensioned such that a lateral aspect of the pivoting gripping arm 850 is seated within the lateral slot 840. The pivoting gripping arm 850 includes a pivot pin 858 which is received within the pin-receiving apertures 842 on the distal insertion head 832 which provides a fixed point for the pivoting gripping arm 850 to rotate in relation to the distal insertion head 832 as the base plate 102 is securely tightened to the plate inserter 818.

The pivoting lever 852 is centrally housed at least partially within the distal insertion head 832 and includes a curved proximal region 860 situated adjacent the distal end of the inner shaft 846, a tapered distal region 862 for engaging with the hex recess 128 in the set screw 126 of the base plate 102, and a spring-loaded pivot mechanism 864.

Figure 43:
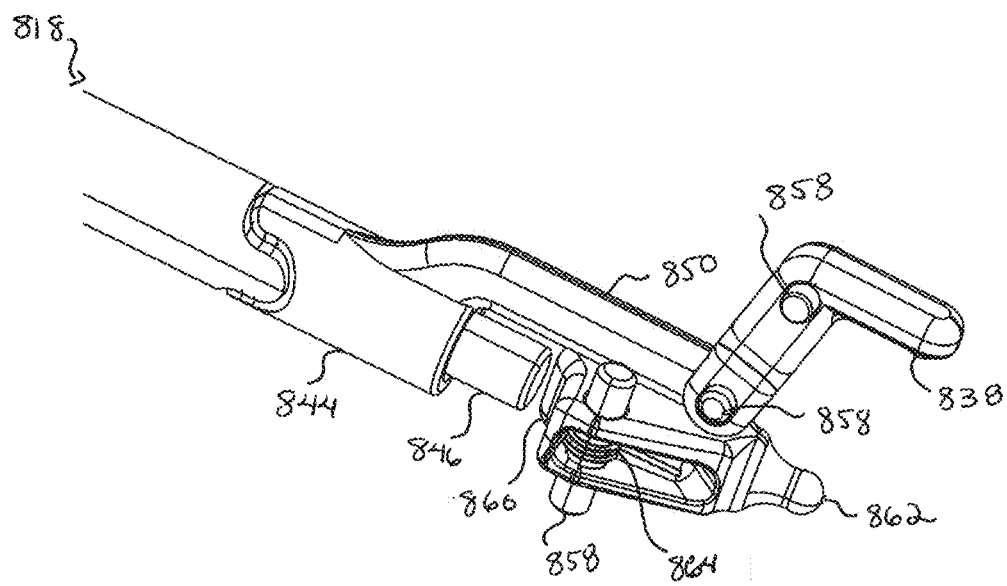
FIG. 43 is a partial perspective view of the distal portion of the plate inserter with the distal insertion head removed.

FIG. 43 depicts the distal portion of the insertion and translation assembly 824 including the distal aspects of the outer and inner shafts 844, 846, pivoting gripping arm 850 and the pivoting lever 852 with the distal insertion head 832 removed for illustrative purposes.

Figure 44:
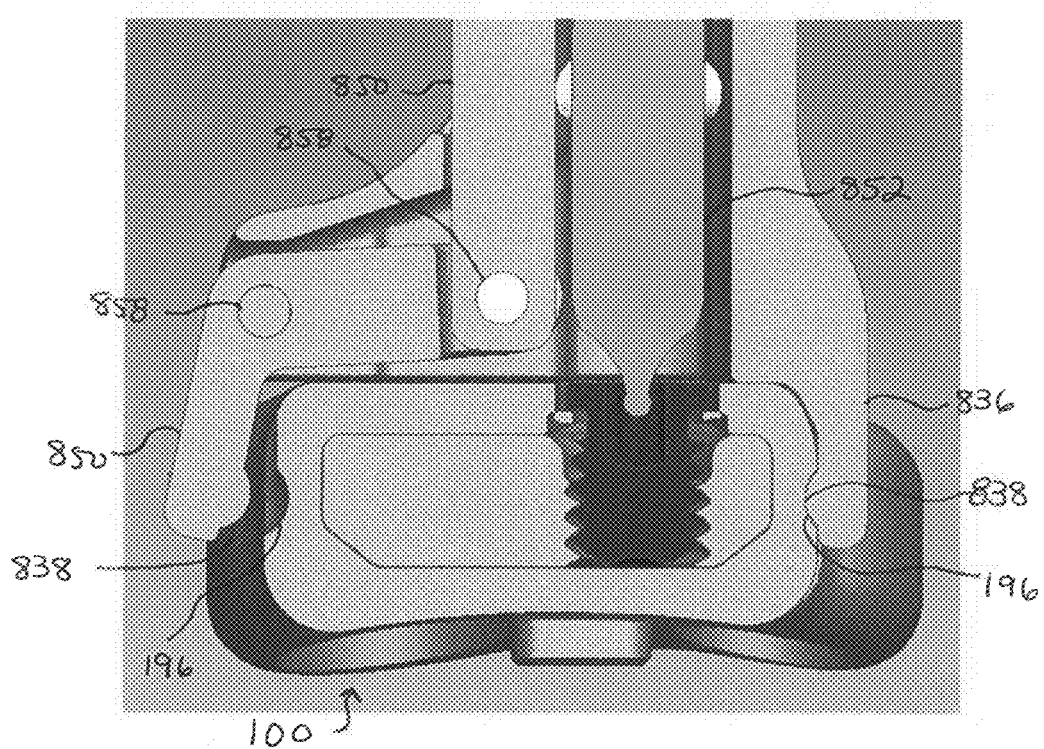
FIG. 44 is a cross-sectional view of the plate inserter of FIG. 37 coupled to the base plate of FIG. 1 with a pivoting gripping arm of the insertion and translation assembly in a first configuration.
Figure 45:
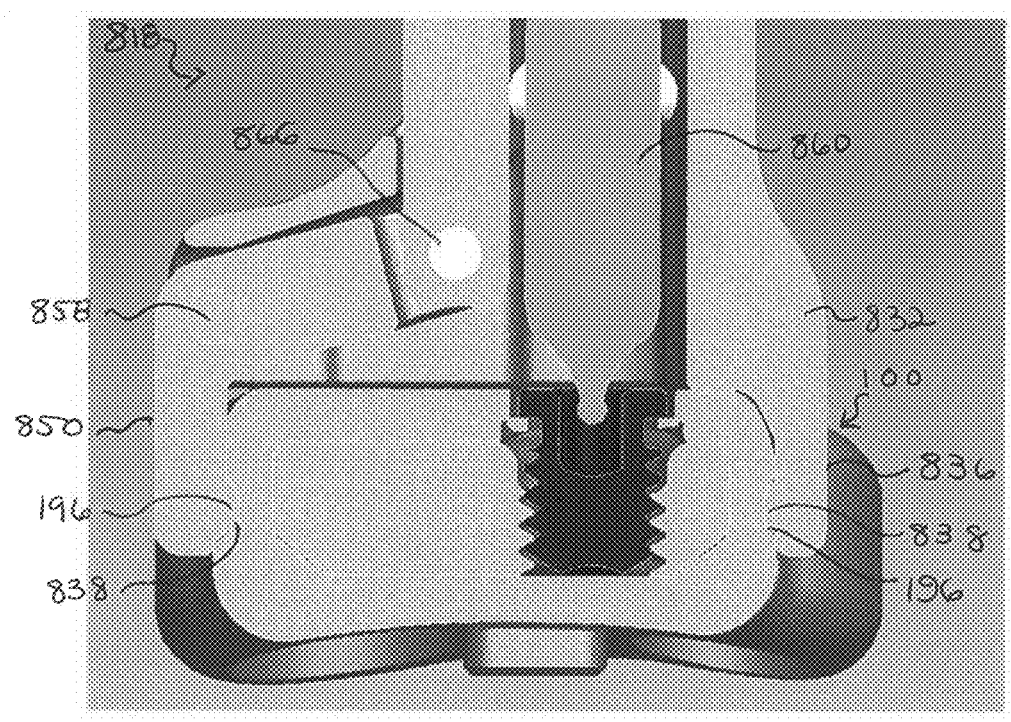
FIG. 45 is a cross-sectional view of the plate inserter of FIG. 37 coupled to the base plate of FIG. 1, with a pivoting gripping arm of the insertion and translation assembly in a second configuration.
Figure 46:
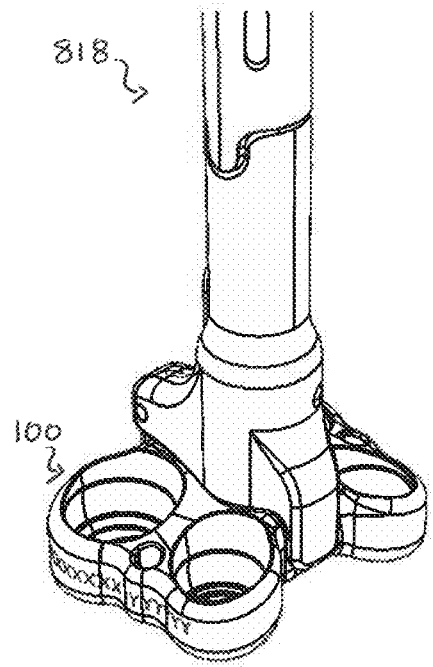
FIG. 46 is a perspective view of the distal end of the plate inserter of FIG. 37 coupled to the base plate of FIG. 1.

Referring to FIGS. 44-46, the step of inserting the base plate 102 into operative corridor will now be described in detail. The pivoting gripping arm 850 is biased in a closed position via a spring loaded mechanism (not shown) but will hinge to the open position with the application of downward pressure. The plate inserter 818 may engage the base plate 102 by placing the plate engagement features 838 of the fixed and pivoting gripping arms 836, 850 adjacent to the engagement features 198 of the base plate 102. The application of downward pressure will force the pivoting gripping arm 150 into an open position such that it may be received into its engagement feature 198. Rotating the first actuating knob 854 clockwise tightens the plate inserter 818 to the base plate 102. With the base plate 102 securely attached to the plate inserter 818, the base plate 102 may then be inserted through the retractor blades 802, 804, 806 and centered over the spinal fusion implant 816 on either side of the vertebral bodies 810, 812. The position of the base plate 102 may then be checked using lateral fluoroscopic imaging.

Figure 47:
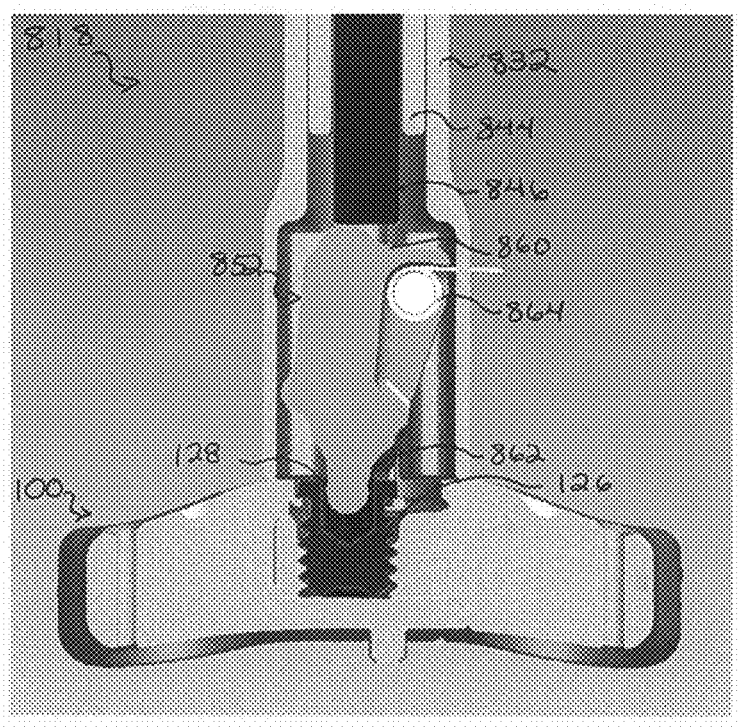
FIG. 47 is a cross-sectional view of the plate inserter of FIG. 37 coupled to the base plate of FIG. 1 with a pivoting lever of the insertion and translation assembly in a first configuration.
Figure 48:
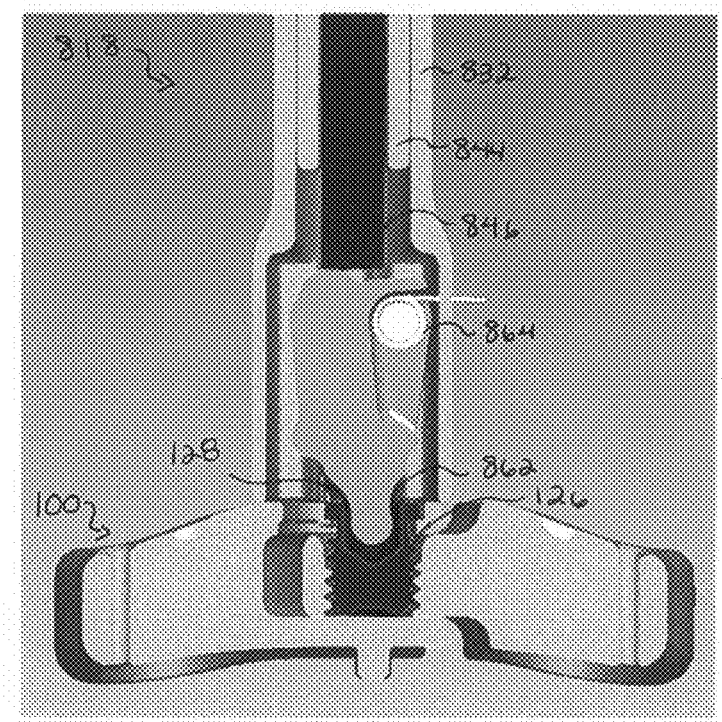
FIG. 48 is a cross-sectional view of the plate inserter of FIG. 37 coupled to the base plate of FIG. 1 with a pivoting lever of the insertion and translation assembly in a second configuration.

Referring now to FIGS. 47-48, the step of lengthening the base plate 102 in situ will now be described in detail. The pivoting lever 150 is biased in a first position by a spring loaded mechanism 864 to keep the base plate 102 in the closed configuration described above. Turning the second actuating knob 856 in the clockwise direction advances the inner shaft 846 towards the curved proximal region 860 of the pivoting lever 150. As the inner shaft 846 is advanced it slides along the top of the curved proximal region and causes it to be displaced and pivot, which in turn causes the tapered distal region 862 to translate within the hex screw recess 128 of the set screw 128 thereby lengthening the base plate 102. With the second actuating knob maximally advanced, the pivoting lever 852 is located in a second position forcing the plate into the open configuration described above. Turning the second actuating knob 856 in the counter-clockwise direction retracts the inner shaft 846 which causes the pivoting lever 852 to return to its biased, first position. A/P fluoroscopic imaging may be used to verify that the base plate 102 is properly centered on the vertebral body and the elongate tubular member 122 is aligned with the disc space 814.

Once the base plate 102 is properly seated within the surgical target site 808, the surgeon proceeds with pilot hole formation to prepare the vertebral bodies 810, 812 for receiving the first bone anchors 104. It is to be appreciated that the plate inserter 818 is still engaged to the base plate 102 during pilot hole formation to ensure that the base plate 102 does not move from its optimal position. Formation of the pilot hole may be accomplished via a number of different techniques and instruments depending upon the surgeon's preference, including but not limited to using drills, taps, awls, etc. to create a pilot hole that is preferably undersized by 1 mm relative to the first bone anchors 104 to be used in order to maximize the purchase of the bone screws 104 within the bone. By way of example only, a self-centering adjustable awl and/or a self-centering adjustable drill may be used to prepare each pilot hole. Fluoroscopic imaging and depth stops on the awl and drill may be utilized during pilot hole formation to ensure proper depth of the pilot hole.

Upon formation of the pilot hole, the bone screws 104 are inserted into the bone. It is to be appreciated that the plate inserter 818 is still engaged to the base plate 102 during the insertion of the bone screws 104 to ensure that the base plate 102 does not move from its optimal position. Insertion of the bone screws 104 may be accomplished via a number of different techniques and instruments depending on the surgeon's preference. Preferably, a screwdriver (not shown) with teeth that complementary to the cutouts 166 of the screw head 152 is used to solidly engage the cutouts 166 of the bone screw 104 for insertion into the bone. The bone screw 104 is then advanced through the pilot hole using A/P fluoroscopy for guidance until the screw head 152 is slightly proud above the base plate 102. The screwdriver may then be removed from the bone screw 104. Pilot hole preparation and bone screw insertion is repeated for the remaining bone screw 104.

After the bone screws 104 are placed, the bone staples 106 may then be placed within the first and second vertebral bodies 810, 812. Bone staples 106 do not require pilot hole preparation and their insertion may be accomplished via number of different techniques and instruments depending on the surgeon's preference. Preferably, a driver capable of delivering a staple (not shown) with teeth complementary to the cutouts on the staple head 204 is used to solidly engage the cutouts of the bone staple 106 for insertion into the bone. According to one embodiment, the intended trajectory of the bone staples 106 is 5° in the anterior-posterior direction and 5° divergent from the endplates of the vertebral body 810 or 812. Using A/P fluoroscopy for depth guidance, the bone staple 106 is then impacted until the staple head 204 is captured within the first spherical pocket 146 of the base plate 102. Staple insertion is repeated for the remaining bone staple 106.

With the bone screws 104 and bone staples 106 positioned, the next step is final tightening of the construct. Tightening of the construct may be accomplished via a number of different techniques and instruments depending upon the surgeon's preference. By way of example, a torque T-handle (preferably with a torque-limiting setting of e.g., 45 in./lb., not shown), may be attached to a driver instrument (not shown) and placed through the distal end of a counter-torque instrument (not shown). The distal hex of the driver instrument may be seated into the lock screw 162 of the bone screw 104. Final tightening may be performed by holding the counter-torque device while rotating the torque T-handle until an audible click is heard. The bone screw 104 will be secured to the base plate 102 via the locking mechanism as described above. This step may be repeated for the remaining bone screw 104 and bone staples 106.

If the surgical bed was broken (angled near the middle) to facilitate access to the disc space during the procedure, it may then be returned to a flat position to ensure maximum axial load (compression) is placed on the spinal fusion implant 816 to facilitate fusion By way of example, the base plate 102 may allow for 2 mm of compression.

Next, the translating locking element 108 may be tightened. By way of example, the translating mechanism may be tightened via the torque/counter-torque method described above by engaging the hex recess 128 of the set screw 126 on the translating locking element 108, holding the plate counter-torque while rotating the torque T-handle clockwise until an audible click is heard. At this point, the construct is fully assembled and locked in place. The surgical retraction system 800, including retractor blades 802, 804, 806 may be closed and removed from the patient. This effectively closes the operative corridor. The procedure being completed, the incision may be stitched up.

While this invention has been described in terms of a best mode for achieving this invention's objectives, it is understood by those skilled in the art that variations may be accomplished in view of these teachings without deviating from the spirit or scope of the invention.

We claim:

1. A system for fixing a first bone segment to a second bone segment, comprising:
   a base plate assembly having a first component and a second component, a locking element, a length defined by a distance between a first end and a second end, a width defined by a distance between a first and a second side, and a thickness defined by a distance between a first surface and a second bone contacting surface, and a plurality of fixation apertures extending between the first surface and the second bone contacting surface,
   wherein the first component comprises the first end and a first abutment surface, the first component comprising a hollow chamber having a top wall, a bottom wall, two side walls, a side opening into the hollow chamber, an enclosed elongated opening passing through the top wall into the hollow chamber, and a first and second engagement feature for engaging with an insertion device at least along a direction perpendicular to the two side walls for inserting the base plate assembly between the first bone segment and the second bone segment, the first engagement feature on a first side wall of the two side walls of the hollow chamber, and the second engagement feature on a second side wall of the two side walls of the hollow chamber opposing the first engagement feature;
   wherein the second component comprises the second end, a second abutment surface, and an insertion portion extending from the abutment surface and configured to be received in the hollow chamber through the side opening, the insertion portion having a threaded aperture extending therethrough that aligns with the elongated opening in the top wall of the first component when the insertion portion is received in the hollow chamber;
   and further wherein the base plate assembly has a first length when the first and second abutment surfaces are positioned adjacent one another, a second length when the first and second abutment surfaces are positioned apart from one another such that the base plate assembly is configured for insertion in a first, closed configuration having the first length and configured for implantation in a second, open configuration having the second length, and wherein the locking element is a set screw engaged in the threaded aperture through the elongated opening and is configured to fixedly engage the first and second components together in the second, open configuration;
   wherein the plurality of fixation apertures comprises a pair of fixation apertures on the first component and a pair of fixation apertures on the second component, wherein the first engagement feature on the first side wall is located between the pair of fixation apertures on the first component and the pair of fixation apertures on the second component, and wherein the first engagement feature sits lower than the first surface and higher than the second bone contacting surface;
wherein the pair of fixation apertures on the first component includes a first fixation aperture having a first diameter along a first direction from the first end to the second end and along a second direction from the first side to the second side and positioned immediately adjacent the first end and the first side, and a second fixation aperture having a second diameter and positioned immediately adjacent the first end and the second side, the first diameter being greater than the second diameter;
wherein the first component further comprises a first recess surrounding the first fixation aperture and a second recess surrounding the second fixation aperture, wherein the first recess is configured to receive a head portion of a first fixation element inserted within the first fixation aperture, and the second recess is configured to receive a head portion of a second fixation element inserted within the second fixation aperture, wherein the system further comprises a plurality of fixation elements including the first fixation element and the second fixation element; and
wherein the system further comprises the insertion device, including:
a proximal end;
a distal end;
a handle disposed proximate the proximal end;
an insertion-translation assembly proximate the distal end and comprising:
a first arm having a first engager engaged with the first engagement feature;
a second arm having a second engager engaged with the second engagement feature; and
a pivot lever with a distal region disposed within the set screw;
a first actuator controllable to disengage one or both of the first and second engager from a respective engagement feature;
a second actuator controllable to move the pivot lever to move the base plate between the closed configuration and the open configuration; and
an elongate element connecting the handle and the insertion-translation assembly and extending perpendicular to the width of the base plate assembly.

2. The system of claim 1, wherein the first recess is spherical.

3. The system of claim 1,
wherein each of the fixation elements comprises:
a bone anchor region; and
a head region comprising:
an upper housing portion that houses a plurality of T-shaped locks disposed within T-slot tracks;
a locking mechanism; and
a bottom portion.

4. The system of claim 3, wherein the plurality of locks are moveable from a first position within the upper housing portion to a second position extending from the upper housing portion.

5. The system of claim 4, wherein the locks are configured for engagement with the first recess in the second position.

6. The system of claim 5, wherein the plurality of locks are moveable radially outwardly from the upper housing portion towards the first recess, wherein the locking mechanism is positioned adjacent the plurality of locks.

7. The system of claim 6, wherein the plurality locks are in the first position when the locking mechanism is in an unlocked position and further wherein the plurality of locks are in the second position when the locking mechanism is in a locked position.

8. The system of claim 1, wherein the bone anchor region is at least one of a threaded shank and a bladed shank.

9. The system of claim 1, wherein the plurality of fixation elements is comprised of two fixation elements with threaded shanks and two fixation elements with bladed shanks.

10. The system of claim 1, wherein the pair of fixation apertures on the second component includes a third fixation aperture having a third diameter along the first direction from the first end to the second end and along the second direction from the first side to the second side and positioned immediately adjacent the second end and the first side, and a fourth fixation aperture having a fourth diameter and positioned immediately adjacent the second end and the second side, the third diameter being greater than the fourth diameter, and the second component further comprising a third recess surrounding the third fixation aperture and a fourth recess surrounding the fourth fixation aperture, wherein the third recess is configured to receive a head portion of a fixation element inserted within the third fixation aperture, and the fourth recess is configured to receive a head portion of a fixation element inserted within the fourth fixation aperture, wherein the first diameter and the third diameter are the same and the second diameter and the fourth diameter are the same.

11. The system of claim 1, wherein each of the first recess and second recess is configured to accommodate a head portion of a fixation element such that said head portion is entirely below the first surface of the base plate assembly.

12. The system of claim 1,
wherein a radius of curvature of the second component at the first end and the first side is different from a radius of curvature of the second component at the first end and the second side, or
wherein a radius of curvature of the first component at the second end and the first side is different from a radius of curvature of the first component at the second end and the second side.

13. The systems of claim 1, wherein the locking element is configured to allow relative movement of the first and second components relative to each other in situ and fixedly engage the first and second components together in the second, open configuration after the base plate assembly is implanted to a desired location relative to the first bone segment and the second bone segment.

14. The system of claim 1, wherein the first engagement feature on the first side wall comprises a first thickness between the first surface and the second bone contacting surface that is smaller than the thickness of the base plate.

15. The system of claim 1,
wherein the handle is non-coaxial with the elongate element;
wherein one or both of the first and second actuator is coaxial with the elongate element;
wherein the first arm is fixed; and
wherein the second arm is configured to pivot responsive to actuation of the first actuator.

16. A system for fixing a first bone segment to a second bone segment, comprising:
a base plate assembly having a first component and a second component, a locking element, a length defined by a distance between a first end and a second end, a width defined by a distance between a first and a second side, and a thickness defined by a distance between a first surface and a second bone contacting surface, and a plurality of fixation apertures extending between the first surface and the second bone contacting surface;

wherein the first component comprises the first end, a first abutment surface, and first portions of the first side and the second side, the first component further comprising a hollow chamber having a top wall, a bottom wall, two side walls, a side opening into the hollow chamber, an enclosed elongated opening passing through the top wall into the hollow chamber, and a first and second engagement feature for engaging with an insertion device at least along a direction perpendicular to the two side walls for inserting the base plate assembly between the first bone segment and the second bone segment, the first engagement feature on a first side wall of the two side walls of the hollow chamber and the second engagement feature on a second side wall of the two side walls of the hollow chamber opposing the first engagement feature;

wherein the second component comprises the second end, a second abutment surface, second portions of the first side and the second side, and an insertion portion extending from the abutment surface and configured to be received in the hollow chamber through the side opening, the insertion portion having a threaded aperture extending therethrough that aligns with the elongated opening in the top wall of the first component when the insertion portion is received in the hollow chamber;

and further wherein the base plate assembly has a first length when the first and second abutment surfaces are positioned adjacent one another, a second length when the first and second abutment surfaces are positioned apart from one another such that the base plate assembly is configured for insertion in a first, closed configuration having the first length and configured for implantation in a second, open configuration having the second length, and wherein the locking element is a set screw engaged in the threaded aperture through the elongated opening and is configured to fixedly engage the first and second components together in the second, open configuration;

wherein the plurality of fixation apertures comprises a pair of fixation apertures on the first component and a pair of fixation apertures on the second component, wherein the first engagement feature on the first side wall is located between the pair of fixation apertures on the first component and the pair of fixation apertures on the second component, and wherein the first engagement feature sits lower than the first surface and higher than the second bone contacting surface;

wherein the pair of fixation apertures on the first component includes a first fixation aperture having a first diameter along a first direction from the first end to the second end and along a second direction from the first side to the second side and positioned immediately adjacent the first end and the first side, and a second fixation aperture having a second diameter and positioned immediately adjacent the first end and the second side, the first diameter being greater than the second diameter;

wherein the system further comprises a plurality of fixation elements; and wherein the system further comprises the insertion device, including:
a proximal end;
a distal end;
a handle disposed proximate the proximal end;
an insertion-translation assembly proximate the distal end and comprising:
a first arm having a first engager engaged with the first engagement feature;
a second arm having a second engager engaged with the second engagement feature; and
a pivot lever with a distal region disposed within the set screw;
a first actuator controllable to disengage one or both of the first and second engager from a respective engagement feature;
a second actuator controllable to move the pivot lever to move the base plate between the closed configuration and the open configuration; and
an elongate element connecting the handle and the insertion-translation assembly and extending perpendicular to the width of the base plate assembly.

17. The system of claim 16, wherein the first component further comprises a first recess surrounding the first fixation aperture and a second recess surrounding the second fixation aperture, wherein the first recess is configured to receive a head portion of a first fixation element inserted within the first fixation aperture, and the second recess is configured to receive a head portion of a second fixation element inserted within the second fixation aperture.

18. The system of claim 16, wherein the pair of fixation apertures on the second component includes a third fixation aperture having a third diameter and positioned immediately adjacent the second end and the first side, and a fourth fixation aperture having a fourth diameter and positioned immediately adjacent the second end and the second side, the third diameter being greater than the fourth diameter.

19. The system of claim 18, wherein the second component further comprises a third recess surrounding the third fixation aperture and a fourth recess surrounding the fourth fixation aperture, wherein the third recess is configured to receive a head portion of a first fixation element inserted within the third fixation aperture, and the fourth recess is configured to receive a head portion of a second fixation element inserted within the fourth fixation aperture, wherein the first diameter and the third diameter are the same and the second diameter and the fourth diameter are the same.

\* \* \* \* \*